US006846636B1

(12) United States Patent
Argraves et al.

(10) Patent No.: US 6,846,636 B1
(45) Date of Patent: Jan. 25, 2005

(54) METHODS AND COMPOSITIONS FOR HDL HOLOPARTICLE UPTAKE RECEPTOR

(75) Inventors: William S. Argraves, Charleston, SC (US); Samar Hammad, Charleston, SC (US); Steingrimur Stefansson, Gaithersburg, MD (US); Bryan Brewer, North Bethesda, MD (US); Alan Remaley, Bethesda, MD (US)

(73) Assignees: American National Red Cross, Falls Church, VA (US); The United States of America as represented by the Department of Health and Human Services, Washington, DC (US); MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 09/700,455

(22) PCT Filed: May 13, 1999

(86) PCT No.: PCT/US99/10619

§ 371 (c)(1),
(2), (4) Date: Feb. 1, 2001

(87) PCT Pub. No.: WO99/60123

PCT Pub. Date: Nov. 25, 1999

Related U.S. Application Data

(60) Provisional application No. 60/085,556, filed on May 15, 1998.

(51) Int. Cl.[7] .................... G01N 33/53; G01N 33/566; G01N 33/92; C12Q 1/62; C07K 14/00

(52) U.S. Cl. .................... 435/7.1; 435/11; 436/501; 436/71; 530/350

(58) Field of Search .................... 435/325, 7.1, 35, 435/11; 436/501, 71; 530/350; 514/2

(56) References Cited

FOREIGN PATENT DOCUMENTS

| WO | WO 90/05744 | 5/1990 |
|----|-------------|--------|
| WO | WO 97/18304 | 5/1997 |

OTHER PUBLICATIONS

Matsumoto, et al, 1997, J. Biol. Chem., 272 (27): 16778–16782.*
Mcknight, et al, 1992, J. Biol. Chem., 267 (17): 12131–12141.*
Hammad, et al, 1999, PNAS, 96: 10158–10163.*
Kolleck, et al, 2002, Am. J. Respir. Cell Mol. Biol., 27: 57–63.*
Varban et al. "Targeted mutation reveals a central role for SR–BI in hepatic selective uptake of high density lipoprotein cholesterol" *Proc. Natl. Acad. Sci.* 95: 4619–4624, Apr. 1998.

Moestrup et al. "The Intrinsic Factor–Vitamin $B_{12}$ Receptor and Target of Teratogenic Antibodies Is a Megalin–binding Peripheral Membrane Protein with Homology to Devlopmental Proteins" *J. Biol. Chem.* 273(9): 5235–5242, Feb. 1998.
Birn et al. "Characterization of an Epithelial ~460–kDa Protein That Facilitates Endocytosis of Intrinsic Factor–Vitamin $B_{12}$ and Binds Receptor–associated Protein" *J. Biol. Chem.* 272(42): 26497–26504, Oct. 1997.
Matsumoto et al. "Cloning and Characterization of $HB_2$, a Candidate High Density Lipoprotein Receptor" *J. Biol. Chem.* 272(27): 16778–16782, Jul. 1997.
Hammed et al. "Interaction of Apolipoprotein J–Amyloid β–Peptide Complex with Low Density Lipoprotein Receptor–related Protein–2/Megalin" *J. Biol. Chem.* 272(30): 18644–18649, Jul. 1997.
Porter et al. "Cholesterol Modification of Hedgehog Signaling Proteins in Animal Development" *Science* 274: 255–259, Oct. 1996.
Willnow et al. "Defective forebrain development in mice lacking gp330/megalin" *Proc. Natl Acad. Sci.* 93: 8460–8464, Aug. 1996.
Stefansson et al. "Glycoprotein 330/Low Density Lipoprotein Receptor–related Protein–2 Mediates Endocytosis of Low Density Lipoproteins via Interaction with Apolipoprotein B100" *J. Biol. Chem.* 270(33): 19417–19421, Aug. 1995.
Kounnas et al. "Identification of Glycoprotein 330 as an Endocytic Receptor for Apolipoprotein J/Clusterin" *J. Biol. Chem.* 270(22): 13070–13075, Jun. 1995.
Kounnas et al. "The Cellular Internalization and Degradation of Hepatic Lipase Is Mediated by Low Density Lipoprotein Receptor–related Protein and Requires Cell Surface Proteoglycans" *J. Biol. Chem.* 270(16): 9307–9312, Apr. 1995.

(List continued on next page.)

Primary Examiner—Elizabeth Kemmerer
Assistant Examiner—Sandra Wegert
(74) Attorney, Agent, or Firm—Needle & Rosenberg, PC

(57) ABSTRACT

The present invention provides an isolated mammalian receptor which specifically binds a high density lipoprotein holoparticle, comprising a subunit of approximately 45–600 kDa molecular weight and one or more subunits selected from the group consisting of a subunit of approximately 40–50 kDa molecular weight, a subunit of approximately 120 kDa molecular weight and a subunit of approximately 400 kDa molecular weight. In addition, the present invention provides a method of screening a substance for the ability to modulate the HDL holoparticle binding and/or internalization activity of the receptor of this invention, comprising: a) contacting the substance with a cell producing a functional HDL receptor; and b) assaying the cell for a modulation of the HDL holoparticle binding and/or internalization activity of the receptor, whereby a modulation of the HDL holoparticle binding and/or internalization activity of the receptor identifies a substance with the ability to modulate the HDL holoparticle binding and/or internalization activity of the ADL receptor.

3 Claims, No Drawings

OTHER PUBLICATIONS

Saito et al. "Complete cloning and sequencing of rat gp330/ "megalin," a distinctive member of the low density lipoprotein receptor gene family" *Proc. Natl. Acad. Sci.* 91: 9725–9729, Oct. 1994.

Kounnas et al. "Glycoprotein 330, a Member of the Low Density Lipoprotein Receptor Family, Binds Lipoprotein Lipase in Vitro" *J. Biol. Chem.* 268(19): 14176–14181, Jul. 1993.

Shen and Angel "Identification of high density lipoprotein binding proteins in mature adipocyte plasma membranes" *Biochem. Cell Biol* 71(7/8): 348–354, 1993.

McKnight et al. "Cloning and Expression of a Cellular High Density Lipoprotein–binding Protein That Is Up–regulated by Cholesterol Loading of Cells" *J. Biol. Chem.* 267(17):12131–12141, Jun. 1992.

Bond et al. "Characterization and purification of proteins which bind high–density lipoprotein" *Biochem. J.* 279:633–641, 1991.

Fyfe et al. "Defective Brush–border Expression of Intrinsic Factor–Cobalamin Receptor in Canine Inherited Intestinal Cobalamin Malabsorption" *J. Biol. Chem.* 266(7): 4489–4494, 1991.

Tozuka and Fidge "Purification and characterization of two high–density–lipoprotein–binding proteins from rat and human liver" *Biochem. J.* 261: 239–244, 1989.

Sahali et al. "Characterization Of A 280–kD Protein Restricted To The Coated Pits Of The Renal Brush Border And The Epithelial Cells Of The Yolk Sac, Teratogenic Effect of the Specific Monoclonal Antibodies" *J. Exp. Med.* 167: 213–218, Jan. 1988.

Murakami et al. "Distinction in the Mode of Receptor–Mediated Endocytosis between High Density Lipoprotein and Acetylated High Density Lipoprotein: Evidence for High Density Lipoprotein Receptor–Mediated Cholesterol Transfer" *J. Biochem.* 101: 729–741, 1987.

* cited by examiner

METHODS AND COMPOSITIONS FOR HDL HOLOPARTICLE UPTAKE RECEPTOR

CROSS-REFERENCE TO RELATED APPLICATIONS

This application is a U.S. National Stage application under 35 U.S.C. § 371 of International Application No. PCT/US99/10619, filed May 13, 1999, which claims benefit of priority from U.S. Provisional Application No. 60/085,556, filed May 15, 1998.

This invention was made with government support under grant number DK45598 awarded by the National Institutes of Health. The government has certain rights in the invention.

BACKGROUND OF THE INVENTION

1. Field of the Invention

The present invention relates to compositions and methods for a high density lipoprotein (HDL) holoparticle uptake receptor for the identification and development of substances (compounds/drugs/therapeutic agents) which modulate the activity and/or expression of the receptor, thereby modulating the uptake of HDL by cells expressing the receptor on the cell surface.

2. Background Art

Epidemiological studies have demonstrated that plasma levels of HDL cholesterol are inversely related to the incidence of coronary heart disease and plasma levels of HDL-cholesterol are useful for predicting an individual's risk of coronary heart disease (Gordon and Rifkind, 1989; Assman and Schulte, 1992). Similarly, levels of Apo-1, the main protein constituent of HDL, are also inversely correlated with cardiovascular disease risk (Stanpfer et al., 1991). Consistent with these studies, is the evidence that HDL has antiatherogenic properties. For example, HDL is known to inhibit oxidation of LDL and transgenic animals having elevated levels of HDL (due to overexpression of ApoA-1) are resistant to high cholesterol diet-induced atherosclerosis (Rubin et al., 1991). Therefore, understanding factors that influence plasma levels of, HDL such as mechanisms of HDL metabolism is of major importance. Unfortunately, there is a poor understanding of HDL catabolism, particularly receptors responsible for mediating the endocytosis and degradation of HDL.

HDL particles are known to facilitate "reverse cholesterol transport," the transport of excess cholesterol from extrahepatic tissues to the liver for repackaging into new lipoproteins, bile acid synthesis, or excretion into the bile (Eisenberg, 1984; Tall, 1990). Tissues such as the adrenal glands, ovaries and testes are also known to use HDL-cholesterol for steroid hormone biosynthesis. In addition, HDL is important in maternal-fetal lipid nutrition, providing cholesterol and lipid soluble vitamins to the placenta, yolk sac and embryo (Woollett, 1996). HDL is thought to have multiple modes of interaction with cells. One interaction process involves HDL particle binding to the liver or steroidogenic tissues, accompanied by transfer of the cholesterol ester without internalization of the particle (selective lipid uptake). Another process involves the HDL particle being internalized, the cholesterol esters removed and the particle being secreted (retroendocytosed) undegraded. However, no receptor has been identified that mediates HDL holoparticle uptake leading to lysosomal degradation.

The present invention overcomes previous shortcomings in the art by providing an HDL holoparticle uptake receptor comprising a complex of proteins and screening methods for identifying substances which modulate the activity and/or expression of the receptor.

SUMMARY OF THE INVENTION

The present invention provides an isolated mammalian receptor which specifically binds a high density lipoprotein holoparticle, comprising a subunit of approximately 450–600 kDa molecular weight and one or more subunits selected from the group consisting of a subunit of approximately 40–50 kDa molecular weight, a subunit of approximately 120 kDa molecular weight and a subunit of approximately 400 kDa molecular weight.

The present invention also provides an isolated mammalian receptor which specifically binds a high density lipoprotein holoparticle, comprising a subunit of approximately 800 kDa molecular weight and one or more subunits selected from the group consisting of a subunit of approximately 40–50 kDa molecular weight, a subunit of approximately 120 kDa molecular weight and a subunit of approximately 400 kDa molecular weight.

Further provided in this invention is an isolated mammalian receptor which specifically binds a high density lipoprotein holoparticle, comprising a subunit of approximately 400 kDa molecular weight and one or more subunits selected from the group consisting of a subunit of approximately 40–50 kDa molecular weight and a subunit of approximately 120 kDa molecular weight.

In addition, the present invention provides an isolated mammalian receptor which specifically binds a high density lipoprotein holoparticle, comprising a subunit of approximately 120 kDa molecular weight and a subunit of approximately 40–50 kDa molecular weight.

Further provided is an isolated polypeptide which specifically binds a high density lipoprotein (HDL) holoparticle and having a molecular weight of approximately 40–50 kDa, an isolated polypeptide which specifically binds a high density lipoprotein holoparticle and having a molecular weight of approximately 120 kDa and an isolated polypeptide which specifically binds a high density lipoprotein holoparticle and having a molecular weight of approximately 400 kDa.

In addition, the present invention provides a method of screening a substance for the ability to modulate the HDL holoparticle binding and/or internalization activity of the receptor of this invention, comprising: a) contacting the substance with a cell producing a functional HDL receptor; and b) assaying the cell for a modulation of the HDL holoparticle binding and/or internalization activity of the receptor, whereby a modulation of the HDL holoparticle binding and/or internalization activity of the receptor identifies a substance with the ability to modulate the HDL holoparticle binding and/or internalization activity of the HDL, receptor.

Furthermore, the present invention provides a method of screening a substance for the ability to modulate the HDL holoparticle binding and/or internalization activity of any of the polypeptides of this invention, comprising: a) contacting the substance with a cell producing a functional polypeptide; and b) assaying the cell for a modulation of the HDL holoparticle binding and/or internalization activity of the polypeptide, whereby a modulation of the HDL holoparticle binding and/or internalization activity of the polypeptide identifies a substance with the ability to modulate the HDL holoparticle binding and/or internalization activity of the polypeptide.

Various other objectives and advantages of the present invention will become apparent from the following detailed description.

DETAILED DESCRIPTION OF THE INVENTION

As used herein, "a" or "an" can mean multiples. For example, "a cell" can mean at least one cell or more than one cell.

The present invention is based on the unexpected and surprising discovery of a mammalian receptor which binds and internalizes an HDL holoparticle. Thus, the present invention provides an isolated mammalian receptor which specifically binds a high density lipoprotein particle, comprising a subunit of approximately 450–600 kDa molecular weight and one or more of the subunits selected from the group consisting of a subunit of approximately 40–50 kDa molecular weight, a subunit of approximately 120 kDa molecular weight and a subunit of approximately 400 kDa molecular weight. The 450–600 kDa subunit, which can appear as a closely spaced doublet on SDS-PAGE under nonreducing conditions, is the protein cubilin, which is a multifunctional receptor capable of binding to several distinct ligands such as intrinsic factor vitamin B 12 complex (Moestrup et al., 1998), immunoglobulin light chains (Batuman et al., 1998) and transferrin.

Additionally, the receptor of this invention can be an isolated mammalian receptor which specifically binds a high density lipoprotein holoparticle, comprising a subunit of approximately 800 kDa molecular weight (which can be a dimer of cubilin) and one or more subunits selected from the group consisting of a subunit of approximately 40–50 kDa molecular weight, a subunit of approximately 120 kDa molecular weight and a subunit of approximately 400 kDa molecular weight.

Particularly, as used herein, the term "HDL receptor" means a polypeptide having a molecular weight of approximately 40–50 kDa, of approximately 120 kDa or of approximately 400 kDa or a complex of 1) a subunit of approximately 450–600 kDa molecular weight or a subunit of approximately 800 kDa molecular weight and 2) at least one and possibly more of the polypeptides described herein, having a molecular weight of approximately 45 kDa, 120 kDa and 400 kDa, wherein the receptor binds an HDL holoparticle (e.g., $HDL_3$) and mediates internalization of the holoparticle to the interior of a cell, where the particle is directed to lysosomal vesicles and/or trafficked elsewhere, including being transcytosed through and out of the cell. The subunits of the HDL receptor may be bound to or otherwise associated with one another or the subunits may be independent of one another.

It is further contemplated that the HDL receptor of this invention can be any combination of the subunits described herein. For example, the HDL receptor can comprise a 450–600 kDa MW subunit and a 40–50 kDa MW subunit; a 450–600 kDa MW subunit, a 40–50 kDa MW subunit and a 120 kDa MW subunit; a 450–600 kDa MW subunit, a 40–50 kDa MW subunit, a 120 kcDa MW subunit and a 400 kDa subunit; a 450–600 kDa MW subunit and a 120 kDa MW subunit; a 450–600 kDa MW subunit, a 120 kDa MW subunit and a 400 kDa MW subunit; a 450–600 kDa MW subunit, a 40–50 kDa MW subunit and a 400 kDa MW subunit; a 450–600 kDa MW subunit and a 120 cDa MW subunit; a 450–600 kDa MW subunit and a 400 kDa MW subunit; a 40–50 kDa MW subunit, a 120 kDa MW subunit and a 400 kDa MW subunit; a 40–50 kDa MW subunit and a 120 kDa MW subunit; a 40–50 kDa MW subunit and a 400 kDa MW subunit; and/or a 120 kDa MW subunit and a 400 kDa MW subunit. The present invention further provides a composition, which can be a complex, comprising a HDL holoparticle bound to or associated with (e.g., by ionic interaction) ahy of the HDL receptors described herein, having any of the possible combinations of subunits described above.

Thus, the present invention further provides an isolated mammalian receptor which specifically binds a high density lipoprotein holoparticle, comprising a subunit of approximately 400 kDa molecular weight and one or more subunits selected from the group consisting of a subunit of approximately 40–50 kDa molecular weight and a subunit of approximately 120 kDa molecular weight.

Additionally provided is an isolated mammalian receptor which specifically binds a high density lipoprotein holoparticle, comprising a subunit of approximately 120 kDa molecular weight and a subunit of approximately 40–50 kDa molecular weight.

The present invention also provides an isolated polypeptide, which specifically binds a high density lipoprotein holoparticle and having a molecular weight of approximately 40–50 kDa. Also provided is an isolated polypeptide, which specifically binds a high density lipoprotein holoparticle and having a molecular weight of approximately 120 kDa. Additionally provided is an isolated polypeptide, which specifically binds a high density lipoprotein holoparticle and having a molecular weight of approximately 400 kDa. Further provided is a composition, which can be a complex, comprising one or more of the HDL-binding polypeptides of this invention bound to or associated with an HDL holoparticle.

The HDL receptor of this invention can be produced in a mouse cell which can be, for example, an F9 teratocarcinoma cell having ATCC accession number CRL1720, which has been treated with $RA/Bt_2cAMP$ to induce the cells to undergo differentiation in culture. The HDL receptor of this invention can also be produced in a rat BN/MSV teratocarcinoma cell (Vandeputte et al., 1979; Le Panse et al., 1995). The receptor of this invention can also be of human origin and is identified and isolated, according to the methods provided herein, from any human cell which produces the HDL receptor of this invention. For example, the human cell of this invention can be, but is not limited to, kidney (e.g., kidney proximal tubule), yolk sac endoderm cells (e.g., extraembryonic endoderm; also known as visceral endodermn), liver, intestine, lung, epididymis, oviduct, brain ependyma, brain choroid plexus, thymus, ileum, placenta and peripheral blood leukocytes (granulocytes, lymphocytes, monocytes/macrophages).

The subunit of the HDL receptor of this invention having a molecular weight of approximately 450–600 kDa is the protein cubilin, having a molecular weight of 460 kDa and having the amino acid sequence as disclosed in Moestrup et al. (1998). Additionally, one of the subunits of the HDL receptor of this invention can be LRP2/megalin (Saito et al., 1994; Stefannson et al., 1995), which may co-migrate with cubilin, and/or a protein in the LDLR family and/or a protein having endocytotic function.

Furthermore, the 450–600 kDa subunit of the HDL receptor of this invention can be the human homologue of the cubilin protein described above. The human homologue is identified in human cells in which it is produced and is isolated according to the methods provided herein. Also, the 40–50 kDa subunit, the 120 kDa subunit and the 400 kDa subunit of the HDL receptor of this invention can be isolated from human cells as taught herein.

With regard to the receptor of this invention, as used herein, "isolated" and/or "purified" means a receptor which is substantially free from the naturally occurring materials with which the receptor is normally associated in nature. Also as used herein, "polypeptide" refers to a molecule comprised of amino acids which correspond to those encoded by a nucleic acid. The HDL receptor subunit polypeptides of this invention can consist of the entire amino acid sequence of the subunit of the HDL receptor or an active (functional) fragment of a subunit polypeptide. Identification of an active fragment can be carried out according to methods well known in the art. The polypeptides or fragments thereof of the present invention are obtained by isolation and purification of the polypeptides from cells where they are produced naturally or by expression of exogenous nucleic acid encoding the subunit polypeptide. Fragments of the subunit polypeptides can be obtained by chemical synthesis of peptides, by proteolytic cleavage of the polypeptide and by synthesis from nucleic acid encoding the portion of interest. The subunit polypeptide may include conservative substitutions where a naturally occurring amino acid is replaced by one having similar properties. Such conservative substitutions do not alter the function of the polypeptide (Lewin, 1994).

Thus, it is understood that, where desired, modifications and changes may be made in the nucleic acid and/or amino acid sequence of the HDL receptor subunit polypeptides of the present invention and still obtain a subunit polypeptide having like or otherwise desirable characteristics. Such changes may occur in natural isolates or may be synthetically introduced using site-specific mutagenesis, the procedures for which, such as mis-match polymerase chain reaction (PCR), are well known in the art.

For example, certain amino acids may be substituted for other amino acids in a subunit polypeptide without appreciable loss of functional activity. Since it is the interactive capacity and nature of a protein that defines that protein's biological functional activity, certain amino acid sequence substitutions can be made in the amino acid sequence (or, of course, the underlying nucleic acid sequence) of the subunit polypeptide and nevertheless obtain an HDL receptor subunit polypeptide with like properties. It is thus contemplated that various changes may be made in the amino acid sequence of the subunit polypeptides (or underlying nucleic acid sequence) without appreciable loss of biological utility or activity and possibly with an increase in such utility or activity. Such activity can be routinely verified.

In addition, the present invention provides a composition comprising the HDL receptor or HDL-binding polypeptide of this invention, bound to or associated with, an HDL holoparticle. Such a receptor/ligand or polypeptide/ligand complex is purified from cells according to methods well known in the art. In addition, purified receptor or HDL-binding polypeptide and purified HDL holoparticle is obtained according to methods well known in the art and combined under standard conditions whereby the receptor or HDL-binding polypeptide and HDL holoparticle can form a complex. Such complexes can be used in the screening methods of this invention.

Furthermore, the HDL receptor or HDL-binding polypeptide of this invention can be in soluble form which can be used in the screening methods of this invention. The soluble HDL receptor or HDL-binding polypeptide can also be used in assays to detect the presence of and determine the quantity of HDL holoparticle in a sarnple and in competitive binding assays to quantitate the amount of HDL receptor or HDL-binding polypeptide in a sample. The soluble HDL receptor or HDL-binding polypeptide can be conjugated to a detectable moiety such as a radioactive moiety, a fluorescence moiety, an enzyme moiety, biotin, and the like, for detection of the receptor or HDL-binding polypeptide, as is well known in the art. In addition, the HDL receptor or HDL-binding polypeptide of this invention in soluble form can be used as an in vivo competitor and to direct drugs and other substances to cells which express the receptor. Fusions of the soluble receptor with drugs may be used as targeting schemes.

The HDL receptor or HDL-binding polypeptide of this invention can be obtained in soluble form according to the methods provided herein for isolating and purifying the HDL receptor or HDL-binding polypeptides and by methods which are standard in the art. The HDL receptor or HDL-binding polypeptide in soluble form can be used in screening assays to identify substances which bind the HDL receptor or HDL-binding polypeptide. Thus, the present invention provides a method of screening a substance for the ability to bind the HDL receptor or HDL-binding polypeptides of this invention, comprising contacting the substance with an HDL receptor or HDL-binding polypeptide and detecting binding of the substance to the HDL receptor or HDL-binding polypeptide. The binding of a substance to the receptor or HDL-binding polypeptide can be determined according to the protocols provided herein and according to methods well known in the art.

Because it is likely that the HDL receptor or HDL-binding polypeptide of this invention is expressed in kidney tubules and therefore, released into urine, the amount of HDL receptor or HDL-binding polypeptide can be measured in the urine according to standard protocols for measuring substances in urine (e.g., using antibodies which bind HDL receptor or HDL-binding polypeptide or using detectable HDL as a ligand). Changes in the amount (e.g., an increase or decrease as compared to a normal control) of HDL receptor or HDL-binding polypeptide in urine can be diagnostic for disorders of HDL metabolism.

The present invention further provides antibodies which specifically bind the HDL receptor or HDL-binding polypeptides of this invention. The antibodies of the present invention include both polyclonal and monoclonal antibodies. Such antibodies may be murine, fully human, chimeric or humanized. These antibodies can also include Fab or F(ab')$_2$ fragments, as well as single chain antibodies (ScFv) (See, e.g., Harlow and Lane, 1989). The antibodies can be of any isotype IgG, IgA, IgD, IgE and IgM. The antibodies can be produced against peptides which are identified to be immunogenic peptides according to methods well known in the art for identifying immunogenic regions in an amino acid sequence. Such antibodies can be produced by techniques well known in the art which include those described in Kohler et al. (1975) or U.S. Pat. Nos. 5,545,806, 5,569,825 and 5,625,126, incorporated herein by reference.

The antibodies of this invention can be used to detect and/or quantitate the HDL receptor or HDL-binding polypeptides of this invention. For example, a method is provided for detecting and/or quantitating a HDL receptor or HDL-binding polypeptide in a sample, which can be a biological sample, comprising contacting the sample with an antibody which specifically binds the HDL receptor or an HDL-binding polypeptide under conditions whereby an antigen/antibody complex can form and detecting the presence of the complex, whereby the presence of the antigen/ antibody complex indicates the presence of HDL receptor or of an HDL-binding polypeptide in the sample. The amount of the HDL receptor or HDL-binding polypeptide in the detected antigen/antibody complex can be determined by methods well known in the art for quantitating protein. The antibodies of this invention can also be screened for the ability to modulate the HDL holoparticle binding and/or internalization activity of the HDL receptor or HDL-binding polypeptides.

Conditions whereby an antigen/antibody complex can form as well as assays for the detection of the formation of an antigen/antibody complex and quantitation of the detected protein are standard in the art. Such assays can include, but are not limited to, Western blotting, immunoprecipitation, immunofluorescence, immunocytochemistry, immunohistochemistry, fluorescence activated cell scanning and/or sorting (FACS), immunomagnetic assays, ELISA, agglutination assays, flocculation assays, cell panning, etc., as are well known to the artisan.

Antibodies which bind the HDL receptor or the HDL-binding polypeptides of this invention can be used to block interaction of HDL with the receptor or HDL-binding polypeptides. In addition, these antibodies can be used to design drugs that interfere with HDL receptor/ligand interaction or HDL-binding polypeptide/HDL interaction, as well as receptor or HDL-binding polypeptide function (e.g., interfere with association among subunits to form an HDL receptor complex capable of binding HDL or mediating its endocytosis). Additionally, antibodies which bind the HDL receptor or HDL-binding polypeptides can be used to lower surface levels of the receptor or HDL-binding polypeptides as a result of a perturbation of receptor recycling by the antibody, as has been shown for low density lipoprotein receptor (LDLR).

Antibodies, as well as other substances identified by the methods provided herein to have the modulating activity of this invention can be used in treatment protocols to modulate the uptake of HDL in a subject to achieve a particular therapeutic effect. Thus, the antibodies and other substances identified as described herein to have modulating activity can be in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Substances identified as having the ability to modulate the activity of the HDL receptor or HDL-binding polypeptides by the methods of this invention can be used, for example, to modulate plasma levels of HDL in a subject, particularly to achieve a benefit from the antiatherogenic properties of HDL (e.g., by raising the level of HDL in a subject). In addition, the HDL receptor modulating substances of this invention can be used to modulate maternal-fetal lipoprotein transport required for delivery of both lipids (e.g., cholesterol and triglycerides) and lipoprotein-associated vitamins (e.g., vitamin A, E and K). In conditions in which embryonic cholesterol metabolism is impaired (e.g., Smith-Lemli-Optix syndrome), augmentation of HDL transport via HDL receptor may overcome cholesterol deficiencies and thereby prevent birth defects.

Furthermore, because the receptor and/or the HDL-binding polypeptide(s) of this invention appear to be present on peripheral blood leukocytes such as monocytes/macrophages, substances such as drugs that modulate activity of the receptor or of the polypeptide(s) can be used to modulate leukocyte growth/function. For example, foam cell formation associated with atherosclerosis can be modulated by substances which modulate activity of the receptor and/or HDL-binding polypeptide(s) of this invention.

To determine the efficacy of administration of the substances identified to have HDL receptor activity modulating capability or HDL-binding polypeptide activity modulating capability according to the methods of this invention, an in vivo radiolabeled-HDL plasma clearance assay can be performed whereby the half-life of radiolabeled-HDL can be measured in a subject in the presence of the substance to determine if the substance is imparting a benefit to the subject by its modulating effect on the HDL receptor or HDL-binding polypoptide.

The present invention further provides an isolated nucleic acid construct comprising a nucleic acid or nucleic acids encoding the subunits of the HDL receptor of this invention and an isolated nucleic acid which selectively hybridizes, under stringent hybridization conditions, with the nucleic acid construct encoding the subunits of the HDL receptor of this invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence (Lewin, 1994). Furthermore, nucleic acids may include codons which represent conservative substitutions of amino acids as are well known in the art.

As used herein, the term "isolated" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids (Michieli et al., 1996). The nucleic acids of this invention can be isolated from cells according to methods well known in the art for isolating nucleic acids. Alternatively, the nucleic acids of the present invention can be synthesized according to standard protocols well described in the literature for synthesizing nucleic acids.

The nucleic acid of this invention can be used as a probe or primer to identify the presence of a nucleic acid encoding a HDL receptor subunit polypeptide in a cell. Thus, the present invention also provides a nucleic acid having sufficient complementarity to the nucleic acid encoding the HDL receptor subunit polypeptides of this invention to selectively hybridize with the subunit-encoding nucleic acid of this invention under stringent conditions as described herein and which does not hybridize nonspecifically with nucleic acids which do not encode the HDL receptor subunit polypeptides under stringent conditions. Thus, the present invention also provides homologues of the disclosed HDL receptor subunits and HDL-binding polypeptides.

"Stringent conditions" refers to the hybridization conditions used in a hybridization protocol or in the primer/ template hybridization in a polymerase chain reaction (PCR) protocol. In general, these conditions should be a combination of temperature and salt concentration for hybridizing and washing chosen so that the denaturation temperature is approximately 5–20° C. below the calculated $T_m$ (melting/denaturation temperature) of the hybrid under study. The temperature and salt conditions are readily determined empirically in routine, preliminary experiments in which samples of reference nucleic acid are hybridized to the primer nucleic acid of interest and then amplified under conditions of different stringencies. The stringency conditions are readily tested and the parameters altered are readily apparent to one skilled in the art. For example, $MgCl_2$ concentrations used in PCR buffer can be altered to increase the specificity with which the primer binds to the template, but the concentration range of this compound used in hybridization reactions is narrow and therefore, the proper stringency level is easily determined. For example, hybridizations with oligonucleotide probes which are 18 nucleotides in length can be done at 5–10° C. below the estimated $T_m$ in 6× SSPE, then washed at the same temperature in 2× SSPE (Sambrook et al., 1989). The $T_m$ of such an oligonucleotide can be estimated by allowing 2° C. for each A or T nucleotide and 4° C. for each G or C. An 18 nucleotide probe of 50% G+C would, therefore, have an approximate $T_m$ of 54° C. Likewise, the starting salt concentration of an 18 nucleotide primer or probe would be about 100–200 mM. Thus, stringent conditions for such an 18 nucleotide primer or probe would be a $T_m$ of about 54° C. and a starting salt concentration of about 150 mM and would be modified accordingly by routine, preliminary experiments. $T_m$ values can also be calculated for a variety of conditions utilizing commercially available computer software (e.g., OLIGO®).

Modifications to the nucleic acids of the invention are also contemplated, provided that the essential structure and function of the HDL receptor subunit polypeptide encoded by the nucleic acid is maintained. Likewise, fragments used as primers can have substitutions, provided that a sufficient number of complementary bases exist to allow for selective amplification, as would be determined by routine experimentation (Kunkel et al., 1987). In addition, nucleic acid fragments used as probes can have substitutions, provided that enough complementary bases exist to allow for hybridization with the reference sequence to be distinguished from hybridization with other sequences, as would be determined by routine experimentation.

The nucleic acids of this invention can be used to produce the HDL receptor subunits and HDL-binding polypeptides of this invention. The nucleic acids can also be used as probes, for example, to screen genomic or cDNA libraries or to identify complementary sequences by Northern, Southern and slot/dot blotting. The nucleic acids of this invention can also be used a primers, for example, to transcribe cDNA from RNA and to amplify DNA according to standard amplification protocols, such as PCR, which are well known in the art and are described in the Examples provided herein. The nucleic acids of this invention can also be used in diagnostic imaging techniques.

Thus, the present invention further provides a method of detecting and/or quantitating the expression of a nucleic acid encoding the HDL receptor subunit polypeptide in a cell by detecting and/or quantitating DNA and/or mRNA in the cell which encodes the subunit polypeptide comprising the steps of: contacting the cell with a detectably labeled nucleic acid probe that hybridizes, under stringent conditions, with DNA and/or mRNA encoding a HDL receptor subunit polypeptide and detecting and/or quantitating the DNA and/or mRNA hybridized with the probe. The mRNA of the cell can be contacted with the probe and detected and/or quantitated according to protocols standard in the art for detecting and quantitating mRNA, including, but not limited to, Northern blotting, dot blotting and PCR amplification. The DNA of the cell can be contacted with the probe and detected and/or quantitated according to protocols standard in the art for detecting and quantitating DNA, including, but not limited to, Southern blotting, dot blotting and PCR amplification. The detection and/or quantitation of DNA or mRNA encoding HDL receptor subunit polypeptides can be used to identify cells which produce the HDL receptor subunit polypeptides of this invention as well as to identify cells which do not produce the HDL receptor subunit, polypeptides of this invention. The former cells can be used directly in the screening methods described herein and the latter can be transfected with nucleic acid encoding the HDL receptor subunit polypeptide or subunit polypeptides of this invention and used in the screening methods of this invention.

The nucleic acid construct comprising nucleic acid encoding the subunits of the HDL receptor of this invention and/or the polypeptides of this invention can be part of a recombinant nucleic acid comprising any combination of restriction sites and/or functional elements as are well known in the art which facilitate molecular cloning and other recombinant DNA manipulations. Thus, the present invention further provides a recombinant nucleic acid comprising a nucleic acid construct comprising nucleic acid encoding one or more of the subunits of the HDL receptor and a recombinant nucleic acid comprising a nucleic acid encoding one or more of the HDL-binding polypeptides of the present invention.

The present invention further provides a vector comprising a nucleic acid construct comprising a nucleic acid encoding one or more of the subunits of the HDL receptor of this invention and/or a vector comprising a nucleic acid encoding one or more of the HDL-binding polypeptides of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, adenovirus, retrovirus and/or adeno-associated virus nucleic acid. The nucleic acid or vector of this invention can also be in a liposome or a delivery vehicle which can be taken up by a cell via receptor-mediated or other type of endocytosis.

The nucleic acid and/or recombinant nucleic acid of this invention can be in a cell, which can be a cell expressing the nucleic acid and/or recombinant nucleic acid whereby a functional HDL receptor or HDL-binding polypeptide is produced and expressed on the surface of the cell. In addition, the vector of this invention can be in a cell, which can be a cell expressing the nucleic acid of the vector whereby a functional HDL receptor or HDL-binding polypeptide is produced and expressed on the surface of the cell.

The present invention further provides a modified cell of a type which normally produces a functional HDL receptor and/or one or more of the functional HDL-binding polypeptides of this invention, wherein a functional HDL receptor and/or one or more of the functional HDL-binding polypeptides is not produced in the cell. By "modified" is meant that the cell has been altered according to methods well known in the art to alter or inhibit the ability of the cell to produce a functional HDL receptor and/or one or more of the HDL-binding polypeptides of this invention. Such modification can be by mutation, antisense treatment, ribozyme treatment and any other treatment now known or identified in the future to alter or inhibit the ability of a cell to produce a functional receptor or polypeptide. The cells of this invention can be in a non-human transgenic animal, as described herein.

The nucleic acid construct comprising a nucleic acid encoding one or more of the subunits of the HDL receptor or the nucleic acid encoding one or more of the HDL-binding polypeptides of this invention can be any nucleic acid that functionally encodes one or more of the subunits or the polypeptides. To functionally encode the subunits or polypeptides (i.e., allow the nucleic acid to be expressed), the nucleic acid can include, for example, expression control sequences, such as an origin of replication, a promoter, an enhancer and necessary information processing sites, such as ribosome binding sites, RNA splice sites, polyadenylation sites and transcriptional terminator sequences. Preferred expression control sequences are promoters derived from metallothionine genes, actin genes, immunoglobulin genes, CMV, SV40, adenovirus, bovine papilloma virus, etc. A nucleic acid encoding selected subunits or polypeptides can readily be determined based upon the genetic code for the amino acid sequence of the selected subunit or polypeptide and many nucleic acids will encode any selected subunit or polypeptide. Modifications in the nucleic acid sequence encoding the subunit or polypeptide are also contemplated. Modifications that can be useful are modifications to the sequences controlling expression of the subunit or polypeptide to make production of the subunit or polypeptide inducible or repressible as controlled by the appropriate inducer or repressor. Such means are standard in the art (see, e.g. Sambrook et al., 1989). The nucleic acids can be generated by means standard in the art, such as by recombinant nucleic acid techniques, as exemplified in the examples herein and by synthetic nucleic acid synthesis or in vitro enzymatic synthesis.

There are numerous *E. coli* (*Escherichia coli*) expression systems known to one of ordinary skill in the art useful for the expression of nucleic acid encoding proteins such as HDL receptor subunit proteins or HDL-binding polypeptides. Other microbial hosts suitable for use include *bacilli*, such as *Bacillus subtilis*, and other *enterobacteria*, such as *Salmonella* and *Serratia*, as well as various *Pseudomonas* species. These prokaryotic hosts can support expression vectors which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the protein sequences. Also, the carboxy-terminal extension of the protein can be removed using standard oligonucleotide mutagenesis procedures.

Additionally, yeast expression can be used. There are several advantages to yeast expression systems. First, evidence exists that proteins produced in a yeast secretion system exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage-signal sequence. The polypeptide coding sequence can be fused in-frame to the pre-pro-alpha-factor leader region. This construct is then put under the control of a strong transcription promoter, such as the alcohol dehydrogenase 1 promoter or a glycolytic promoter. The protein coding sequence is followed by a translation termination codon, which is followed by transcription termination signals. Alternatively, the polypeptide coding sequence of interest can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Efficient post-translational glycosylation and expression of recombinant proteins can also be achieved in Baculovirus systems in insect cells.

The HDL receptor subunits and polypeptides of this invention can be expressed in mammalian cells. Mammalian cells permit the expression of proteins in an environment that favors important post-translational modifications such as folding and cysteine pairing, addition of complex carbohydrate structures and secretion of active protein. Vectors useful for the expression of proteins in mammalian cells are characterized by insertion of the protein coding sequence between a strong viral promoter and a polyadenylation signal. The vectors can contain genes conferring either gentamicin or methotrexate resistance for use as selectable markers. The subunit protein coding sequence can be introduced into a Chinese hamster ovary (CHO) cell line using a methotrexate resistance-encoding vector. Presence of the vector RNA in transformed cells can be confirmed by Northern blot analysis and production of a cDNA or opposite strand RNA corresponding to the subunit or polypeptide coding sequence can be confirmed by Southern and Northern blot analysis, respectively. A number of other suitable host cell lines capable of secreting intact proteins have been developed in the art and include the CHO cell lines, HeLa cells, myeloma cell lines, Jurkat cells and the like. Expression vectors for these cells can include expression control sequences, as described above.

The vectors containing the nucleic acid sequences of interest can be transferred into the host cell by well-known methods, which vary depending on the type of cell host. For example, calcium chloride transfection is commonly utilized for prokaryotic cells, whereas calcium phosphate treatment or electroporation may be used for other cell hosts.

Alternative vectors for the expression of protein in mammalian cells, similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been positioned to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

The present invention further provides a method of producing the HDL receptor or the HDL-binding polypeptide of this invention, comprising culturing the cells of the present invention which contain a nucleic acid construct comprising nucleic acid encoding the HDL receptor subunits and/or a nucleic acid encoding a HDL-binding polypeptide under conditions whereby the nucleic acid is expressed and the HDL receptor and/or polypeptides are produced. Conditions whereby the HDL receptor and/or HDL-binding polypeptides are produced can include the standard conditions of any expression system, either in vitro or in vivo, in which the HDL receptor and/or, polypeptides of this invention are produced in functional form. By "functional" is meant that the HDL receptor and/or the HDL-binding polypeptides are expressed on the surface of cells and act to bind HDL particles and mediate their internalization, leading to either lysosomal degradation or subcellular trafficking, including transcytosis. For example, protocols describing the conditions whereby nucleic acids encoding the HDL receptor and the HDL-binding polypeptides of this invention are expressed are provided in the Examples section herein. The receptor and/or polypeptides can be isolated and purified from cells according to methods standard in the art.

As stated above, the present invention further contemplates a transgenic animal in which the function of the HDL receptor of this invention is altered as compared with the function of the HDL receptor of this invention in a non-transgenic animal of the same species. As used herein, "transgenic animal" describes a non-human animal which has been altered to 1) produce one or more of the subunits of the HDL receptor of this invention in an animal that would normally not produce one or more of the subunits of the HDL receptor; 2) produce one or more of the subunits of the HDL receptor of this invention in greater amounts than the animal would normally produce; or 3) no longer produce one or more of the subunits of the HDL receptor of this invention in a functional form in an animal that would normally produce one or more of the subunits of the HDL receptor of this invention in a functional form. Such transgenic animals can be produced according to methods well known in the art and as described herein for introducing exogenous DNA into the germ line of an animal or "knocking out" a functional gene product. The transgenic animals of this invention can be used in the screening methods described herein to identify substances which modulate the binding and/or internalization activity of the HDL receptor.

Thus, the present invention further provides an animal which normally produces a high density lipoprotein holoparticle receptor, wherein a functional high density lipoprotein holoparticle receptor is not produced.

Also provided in this invention is a method of screening a substance for the ability to modulate the HDL holoparticle binding and/or internalization activity of the HDL receptor of this invention, comprising: a) contacting the substance with a cell producing a functional HDL receptor; and b) assaying the cell for a modulation of the HDL holoparticle binding and/or internalization activity of the receptor, whereby a modulation of the HDL holoparticle binding and/or internalization activity of the receptor identifies a substance with the ability to modulate the HDL holoparticle binding and/or internalization activity of the HDL receptor.

Also provided is a method of screening a substance for the ability to modulate the HDL holoparticle binding and/or internalization activity of an HDL-binding polypeptide, comprising: a) contacting the substance with a cell producing a functional HDL-binding polypeptide; and b) assaying the cell for a modulation of the HDL holoparticle binding and/or internalization activity of the polypeptide, whereby a modulation of the HDL holoparticle binding and/or internalization activity of the polypeptide identifies a substance with the ability to modulate the HDL holoparticle binding and/or internalization activity of the HDL-binding polypeptide of this invention. It is understood that the cell of this method can produce one or more than one of the HDL-binding polypeptides of this invention. Identification of which of the HDL-binding polypeptides of this invention are produced by a cell can be carried out according to methods standard in the art and as described in the Examples provided herein.

The HDL holoparticle binding and/or internalization activity of the HDL receptor and HDL-binding polypeptide of this invention can be assayed according to methods well known in the art, such as the [$^{125}$I]-HDL internalization and degradation assay, the assay for DiI-HDL uptake measured by fluorescence activated cell scanning and the assay for laser scanning confocal fluorescence microscopy, which are provided in the Examples herein. Other assays for assessing the binding and/or internalization function of the HDL receptor and HDL-binding polypeptide of this invention can include, but are not limited to, an HDL holoparticle binding assay, an HDL holoparticle internalization assay, an HDL holoparticle degradation assay, an HDL receptor or HDL-binding polypeptide degradation assay, an assay which detects modulation in the HDL holoparticle binding and/or internalization activity of the receptor and HDL-binding polypeptide as a result of an increase or decrease in the amount of HDL receptor-encoding and HDL-binding polypeptide-encoding mRNA produced by a cell; an assay which detects modulation in the HDL holoparticle binding and/or internalization activity of the protein as a result of an increase or decrease of the total amount of the HDL receptor and HDL-binding polypeptide produced by a cell; a receptor recycling and polypeptide recycling assay; and any other assay now known or later developed whereby the HDL binding and/or internalization activity of the HDL receptor and HDL-binding polypeptide of this invention can be determined.

In particular, it is contemplated that the ability of a substance to modulate the HDL binding and/or internalization activity of the HDL receptor and HDL-binding polypeptide can be determined by assaying for binding and/or internalization of HDL at the cell surface, as well as by assaying for transcription of the genes encoding the subunits of the HDL receptor and/or the HDL-binding polypeptides and/or translation of the subunits of the HDL receptor and/or the HDL-binding polypeptides of this invention. Methods for quantitating nucleic acid and/or protein in a cell are well known in the art and are taught herein. Thus, the present invention provides a method of screening a substance for the ability to modulate the HDL holoparticle binding and/or internalization activity of the HDL receptor and/or the HDL-binding polypeptides of this invention, comprising: a) contacting the substance with a cell producing a functional HDL receptor and/or one or more of the HDL-binding polypeptides of this invention; and b) assaying the cell for a modulation of the HDL holoparticle binding and/or internalization activity of the receptor and/or one or more of the HDL-binding polypeptides by measuring the amount of HDL receptor-encoding mRNA and/or the amount of HDL-binding polypeptide-encoding mRNA in the cell, whereby a decrease or increase in the amount of HDL receptor-encoding mRNA and/or in the amount of HDL-binding polypeptide-encoding mRNA in the cell as compared with the amount of HDL receptor-encoding mRNA and/or HDL-binding polypeptide-encoding mRNA in a cell not contacted with the substance identifies a substance having the ability to modulate the HDL holoparticle binding and/or internalization activity of the HDL receptor and/or HDL-binding polypeptides of this invention. Such a substance would have the ability to modulate activity at the level of transcribing HDL receptor-encoding mRNA and/or HDL-binding polypeptide-encoding mRNA in a cell.

Furthermore, the present invention provides a method of screening a substance for the ability to modulate the HDL holoparticle binding and/or internalization activity of the HDL receptor and/or one or more of the HDL-binding polypeptides of this invention, comprising: a) contacting the substance with a cell producing a functional HDL receptor and/or one or more of the HDL binding polypeptides of this invention; and b) assaying the cell for a modulation of the HDL holoparticle binding and/or internalization activity of the receptor and/or HDL-binding polypeptide by measuring the amount of HDL receptor and/or the amount of one or more of the HDL-binding polypeptides of this invention produced by the cell, whereby a decrease or increase in the amount of HDL receptor and/or the amount of one or more of the HDL-binding polypeptides of this invention produced by the cell as compared with the amount of HDL receptor and/or HDL-binding polypeptides produced by a cell not contacted with the substance identifies a substance having the ability to modulate the HDL holoparticle binding and/or internalization activity of the HDL receptor and/or HDL-binding polypeptides of this invention. Such a substance would have the ability to modulate activity at the level of translating HDL receptor-encoding mRNA and/or HDL-binding polypeptide-encoding mRNA into a functional HDL receptor and/or functional HDL-binding polypeptides.

The present invention further provides a method of screening a substance for the ability to modulate the HDL holoparticle binding and/or internalization activity of the HDL receptor or one or more of the HDL-binding polypeptides of this invention, comprising: a) contacting the substance with a cell producing a functional HDL receptor or one or more of the HDL-binding polypeptides of this invention; and b) assaying the cell for a modulation of the HDL holoparticle binding and/or internalization activity of the receptor or polypeptide(s) by measuring the rate at which an HDL receptor or polypeptide returns to the cell surface following endocytosis, whereby an increase or decrease in the rate at which an HDL receptor or polypeptide returns to the surface of a cell contacted with the substance, as compared with the rate at which an HDL receptor or polypeptide returns to the surface of a cell not contacted with the substance identifies a substance having the ability to modulate the HDL holoparticle binding and/or internalization activity of the HDL receptor or one or more of the HDL-binding polypeptides of this invention. Such recycling protocols are well known in the art. Such a substance would have the ability to modulate activity at the level of modulating the rate of recycling of the HDL receptor or HDL-binding polypeptide, thereby effecting the number of receptors or HDL-binding polypeptides on the surface of a cell.

Further provided is a method of screening a substance for the ability to modulate the RDL holoparticle binding and/or internalization activity of the HDL receptor or one or more of the HDL-binding polypeptides of this invention, comprising: a) contacting the substance with a cell producing a functional HDL receptor or one or more HDL-binding polypeptides of this invention; and b) assaying the cell for a modulation of the HDL holoparticle binding and/or internalization activity of the receptor or HDL-binding polypeptide by measuring the half life of the HDL receptor or HDL-binding polypeptide (e.g., its rate of degradation), whereby a decrease or increase in the half life of the HDL receptor or HDL-binding polypeptide produced by the cell as compared with the half life of an HDL receptor or HDL-bind ing polypeptide produced by a cell not contacted with the substance identifies a substance having the ability to modulate the HDL holoparticle binding and/or internalization activity of the HDL receptor or HDL-binding polypeptide. Such a substance would have the ability to modulate activity by modulating the rate of turnover of the HDL receptor or HDL-binding polypeptide.

The cells of the screening methods of this invention can be any cell which produces the HDL receptor and/or one or more of the HDL-binding polypeptides of this invention, either naturally or by transfection with a nucleic acid construct comprising nucleic acid expressing the subunits of the HDL receptor as well as by transfection with nucleic acid encoding one or more of the HDL-binding polypeptides of this invention. Such cells can be, but are not limited to, F9 cells treated with RA/Bt$_2$cAMP to induce differentiation, rat yolk sac crrdoderrn cells (e.g., ATCC No. CRL-2180), mouse yolk sac endoderm cells (e.g. ATCC No. CRL-2069), chicken yolk sac endoderm cells (e.g., ATCC No. CRL-2188), mouse endoderm cells (e.g., ATCC No. 1720), primary yolk sac cells, kidney cells, lung epithelial cells, cells of the male and female reproductive tract (epididymis, oviduct), brain ependyma, Brown Norway rat yolk sac epithelial cells transformed with sarcoma virus, trophoblastic cells (Sahali et al., 1992), intestinal epithelial cells (Birn et al., 1997), BN/MSV cclls and brain choroid plexus cells, as well any other cells now known or later identified to produce the HDL receptor and/or HDL-binding polypeptides of this invention, including cells transfected with HDL receptor-encoding nucleic acid and HDL-binding polypeptide-encoding nucleic acid.

The present invention is more particularly described in the following examples which are intended as illustrative only since numerous modifications and variations therein will be apparent to those skilled in the art.

EXAMPLES

Example 1

Characterization of the HDL Receptor
Lipoproteins
DiI-labeled human HDL was purchased from Biomedical Technologies (Stoughton, Mass.). Human HDL, delipidated-HDL (apoHDL) and LDL were prepared as described previously (Brewer et al., 1986). DiI-HDL and HDL were depleted of apoE-HDL and other heparin-binding particles according to the procedure of Oram (1986), dialyzed against 150 mM NaCl, 50 mM Tris pH 7.4 (TBS) containing 2 mM EDTA, filter sterilized and stored at 4° C. Lipoprotein concentration was determined using a BCA protein assay (Pierce, Rockford, Ill.).
Cells
Mouse embryonal teratocarcinoma F9 cells (ATCC CRL 1720) were obtained from American Type Culture Collection and grown in plates coated with 0.1% gelatin, in Dulbecco's modified Eagle's media (DMEM, Gibco) supplemented with 10% iron-fortified bovine calf serum (BCS) (Hyclone, Logan, Utah), penicillin, and streptomycin. Differentiation of the F9 cells was performed essentially as described previously (Stefansson et al., 1995; Kounnas et al., 1995). F9 cells were seeded onto gelatin-coated 150 mm plates (Corning, Corning, N.Y.) at $1 \times 10^2$ cells/cm$^2$ in DMEM containing 10% BCS, 0.1 M retinoic acid (RA) (Calbiochem, San Diego, Calif., diluted from a 0.1 M stock in DMSO) and 0.2 μM dibutyryl cyclic AMP (Bt$_2$cAMP) (Sigma, diluted from a 0.1 M stock in DMSO). The cells were then grown at 37° C., 5% CO$_2$ for 6 days without change of medium.

[$^{125}$I]-HDL Internalization and Degradation Assay

HDL internalization and degradation assays were performed in a manner similar to LDL and apolipoprotein J internalization and degradation assays described previously (Stefansson et al., 1995; Kounnas et al., 1995). ApoE-free HDL (HDL$_3$) was labeled with [$^{125}$I]-iodine using the iodine monochloride method (Goldstein et al., 1983). RA/Bt$_2$cAMP-treated and -untreated F9 cells were seeded onto gelatin-coated 3.83 cm$^2$ wells (Corning, Corning, N.Y.) at $1.5-1.75 \times 10^5$ cells/well and allowed to grow for 18 h at 37° C., 5% CO$_2$. Prior to the addition of [$^{125}$I]-HDL, the cells were washed with serum-free DMEM and incubated in the assay medium (DMEM, 20 mM HEPES, ITS, penicillin/streptomycin, and 1.5% BSA) containing unlabeled HDL$_3$ (80 μg/ml), RAP (1 μM), chloroquine (50 μM) (Sigma) or BSA (10 μM) and incubated for 0.5 hours at 37° C., 5% CO$_2$. The medium was then removed and [$^{125}$I]-HDL$_3$ (2 μg/ml) in serum-free medium or in serum-free medium containing unlabeled HDL$_3$ (80 μg/ml), RAP (1 μM), chloroquine (50 μM) or BSA (10 μM) was added and incubated with the cells for 6.5 h at 37° C., 5% CO$_2$. The conditioned culture medium was treated with trichloroacetic acid (final concentration 10%) and centrifuged at 10,000×g for 10 min. The amount of radioactivity present in the supernatant was taken to represent the amount of degraded HDL (Goldstein and Brown, 1974). The cell layer was washed three times with cold (4° C.) dPBS and then treated with 0.5 mg/ml trypsin-0.5 mM EDTA (Mediatech, Washington, D.C.), 50 μg/ml proteinase K (Sigma) in dPBS for 2–4 min at 4° C. The released cells were pelleted by centrifugation at 1,000×g for 15 min and the amount of radioactivity in the cell pellet measured.

It was during the course of evaluating lipoprotein uptake and degradation by LRP-2 expressed by RA/B$_2$cAMP differentiated F9 cells that the discovery was made that the treated F9 cells were also capable of mediating uptake of HDL. This observation was followed up on by using radio-iodinated HDL to evaluate the ability of the treated F9 cells to internalize and degrade HDL. These studies demonstrated that RA/Bt$_2$cAMP-treated F9 cells internalized and degraded [$^{125}$I]-HDL and that this activity was not observed in untreated F9 cells. Excess unlabeled HDL inhibited both processes. The degradation of HDL occurred in lysosomes, as evidenced by the fact that chloroquine, a drug that inhibits lysosomal proteinase activity, could effectively block the degradation. Furthermore, the protein, RAP, a 39 kDa chaperone protein that inhibits ligand binding to LDLR family members (Battey et al., 1994; Bu et al., 1995; Herz et al. 1991; Kounnas et al., 1992; Williams et al. 1992), inhibited the endocytosis and degradation of [$^{125}$I]-HDL.

Laser Scanning Confocalfluorescence Microscopy

Cells were plated into gelatin-coated wells of 8-well plastic chamber slides (Nalge Nunc, Naperville, Ill.) ($4 \times 10^4$ cells/cm$^2$) and incubated at 37° C., 5% CO$_2$ for 2 hours. The cells were washed with serum-free DMEM and incubated in serum-free DMEM containing ITS (insulin 5 μg/ml, transferrin 5 μg/ml, sodium selenite 5 ng/ml, Boehringer Mannheim, Germany), penicillin, and streptomycin for 18 hours at 37° C., 5% CO$_2$. Prior to addition of DiI-HDL, the cells were incubated with serum-free DMEM containing unlabeled HDL$_3$ (40 μg/ml) or RAP (1 μM) for 0.5 hour at 37° C., 5% CO$_2$. DiI-HDL (1 μg/ml) in serum-free DMEM or in serum-free DMEM containing unlabeled HDL$_3$ (40 μg/ml) or RAP (1 μM) was then incubated with the cells for 2–4 hours at 37° C., 5% CO$_2$. The cells were washed three times with Dulbecco's phosphate buffered saline (dPBS), fixed in 3% formaldehyde in dPBS for 20 minutes at room temperature. After rinsing with dH$_2$O, mounting medium (Vectashield, Vector Laboratories, Burlingame, Calif.) was added and coverslips applied and sealed with cement (Pfaltz & Bauer, Waterbury, Conn.). The cells were examined using a BiORad MRC1000 laser scanning confocal microscope.

Results of studies carried out as described above demonstrated that the RA/B2$_2$cAMP treated F9 cells, but not the untreated F9 cells, were capable of internalizing HDL labeled with DiI (a fluorescent lipid), producing a punctate intracellular staining pattern consistent with endocytotic vesicle localization, indicating that the diI-HDL is endocytosed in a manner similar to LDL. The uptake of DiI-HDL could be completely blocked by addition of the antagonist, RAP, but not by excess LDL.

Measuremnent of DiI-HDL Uptake by Fluorescence-Activated Cell (FAC) Scanning

Untreated and RA/Bt$_2$cAMP-treated F9 cells ($1-1.5 \times 10^5$ cells/cm$^2$) were grown for 18 hours in serum-free medium (DMEM, ITS, penicillin, and streptomycin). After washing the cell layers with the same serum-free medium, apoE-free DiI-HDL was added to a final concentration of 1 μg/ml and incubated for 1–2 hours at 37° C., 5% CO$_2$. For competition experiments, competitors were added in serum-free medium and incubated for 0.5 hours at 37° C., 5% CO$_2$ prior to the addition of the DiI-HDL. After the incubation, the medium was removed, cell layers washed with serum-free medium and the cells released with a 0.5 mg/ml trypsin-0.53 mM EDTA solution (Mediatech). The cells were then pelleted by centrifugation at 180×g and resuspended in DMEM. Twice more, the cells were pelleted by centrifugation at 180×g, and resuspended in dPBS. The cells were then subjected to FAC sorting on a FACStarplus instrument (Becton Dickinson, San Jose, Calif.).

The results of experiments in which FAC scanning was performed on treated F9 cells that had been incubated with DiI-HDL and various competitors revealed that approximately 25% of the treated F9 cells internalized the labeled HDL. The uptake of the DiI-HDL could be blocked by HDL and RAP similar to what was observed in the assays described above. These results indicate that the RA/Bt$_2$cAMP treatment induces the HDL uptake phenotype in a subpopulation of the F9 cells. Fluorescence activated cell sorting or magnetic bead panning can be employed with the markers described herein (e.g., DiI-HDL for FAC sorting and HDL conjugated to Tosyl-activated magnetic beads (Dynabeads, Dynal) according to methods standard in the art to obtain a homogenous population of cells displaying the HDL uptake phenotype. Aliquots of cells selected by either approach can be incubated with DiI-HDL and subjected to FAC scanning analysis to evaluate the extent of the enrichment in cells capable of mediating HDL uptake as compared with unsorted cells. The stability of this phenotype can also be evaluated by maintaining the sorted cells in expanded cultures. Such homogenous populations would be useful for purifying components of the receptor of this invention and in the screening methods employing this receptor.

Additional experiments were conducted which were designed to evaluate the specificity of HDL uptake exhibited by the differentiated F9 cells. In particular, internalization of HDL was evaluated in the presence of a variety of substances, such as ApoAI, ApoAII and ApoE2, which are the major apolipoprotein components of HDL. The ability of these apolipoproteins to inhibit HDL uptake is an indication that the HDL receptor interacts with each of these proteins.

Also, heparin and heparinase are important because HDL uptake is known to be associated with a secretion-recapture mechanism whereby hepatic lipase is secreted and becomes associated with HDL and then through a process involving cell surface heparin sulfate-containing proteoglycans, the HDL-hepatic lipase complex becomes internalized. That heparin and heparinase treatment did not block HDL uptake indicates that the mechanism does not involve cell surface proteoglycans and is therefore a process distinct from the hepatic lipase-dependent mechanism.

Fucoidan is a ligand for a number of scavenger receptors, as is oxidized LDL (Ox-LDL). The inability of these ligands to block HDL uptake indicates that scavenger receptors are not involved in the uptake process.

Aprotinin is a LRP-2/megalin ligand, as is LDL and VLDL (very low density lipoprotein). The inability of these ligands to block HDL uptake suggests that LRP2/megalin is not involved in the process. However, an HDL binding site may exist on LRP-2/megalin that is distinct from the binding sites of LDL and aprotinin. Therefore, the inability of these reagents to compete does not conclusively eliminate LRP-2 megalin/gp330 as playing a role in the process of HDL uptake. Furthermore, given the fact that megalin has been detected in the HDL-Sepharose eluates from treated F9 cell extracts, it is possible that megalin may be associated with the HDL receptor complex, perhaps acting as a co-receptor. Ovalbumin was included as a control.

In an additional FAC scanning experiment, the cell binding and uptake of DiI-HDL was completely blocked by the addition of excess unlabeled HDL or the antagonist RAP, but not by LDL. It can be concluded from these data that the RA/Bt$_2$cAMP-treated F9 cells express an HDL holoparticle endocytosis receptor.

HDL-Sepharose Affinity Chromatography

HDL-Sepharose affinity chromatography was performed using detergent extracts of RA/Bt$_2$cAMP-treated and -untreated F9 cells that were either cell surface [$^{125}$I]-labeled or non-radiolabeled. Cells (1×10$^8$) were radioiodinated using the lactoperoxidase/glucose oxidase method (Ashcom et al., 1990). After labeling, the cells were resuspended in 50 mM octyl-β-D-glucopyranoside (Calbiochem), TBS, containing 1 mM CaCl$_2$, 1 mM MgCl$_2$, 2 mM PMSF (OG buffer) and passed repeatedly through a 21 gauge needle. The extract was clarified by centrifugation at 100,000×g using a Sorvall RC-70 centrifuge and an AH650 rotor. Extracts from each cell type were applied to columns of Sepharose-CL4B (5 ml) (Pharmacia) equilibrated with the OG buffer. Sepharose CL4B-absorbed extracts were applied to columns of apoHDL coupled to CNBr-activated-Sepharose (10 mg protein/ml resin). The columns were washed with OG buffer and the bound proteins eluted with sequential applications of IM, 4M and 8 M urea buffer containing 50 mM Tris pH 7.4.

Non-radiolabeled cells (1×10$^9$) were washed three times with divalent cation-free dPBS and detached using a 2 mM EDTA in divalent cation-free dPBS. The released cells were pelleted by centrifugation at 180×g and the cell pellets resuspended in DMEM. The centrifugation and resuspension process was repeated several times (twice with DMEM and twice with DPBS) and the cells finally resuspended in 0.25 M sucrose, 10 mM Hepes pH 7.4, containing a protease inhibitor cocktail (Complete™, Mini EDTA-free, Boehringer Mannheim, Indianapolis, Ind.). The cells were homogenized on ice using a Polytron homogenizer (Kinematica AG, Switzerland) at full speed for 2×30 seconds and the homogenates centrifuged at 2,000×g using a Sorvall RC-5B ultracentrifuge and a SS-34 rotor. The resulting supernatants were centrifuged at 100,000×g for 1 hour using a Sorvall RC-70 ultracentrifuge and an AH629 rotor. The pellets were resuspended in 2 ml of CHAPS buffer (20 mM CHAPS, TBS, 1 mM PMSF) by repeated passage through a 21-gauge needle. The extract was clarified by centrifugation at 100,000×g for 1 hour using an AH-650 rotor. The concentration of protein in the final supernatants was determined and equal amounts of protein (~20 mg) from each cell type was applied to columns of Sepharose-CL4B (5 ml) (Pharmacia) equilibrated with extraction buffer. The Sepharose CL4B flow through solutions were applied to 6 ml columns of apoHDL coupled to CNBr-activated-Sepharose (10 mg protein/ml resin) and incubated 18 h at 4° C. with nutational movement. The columns were washed with extraction buffer and bound proteins eluted with 8 M urea buffer-containing 50 mM Tris pH 7.4.

HDL-Sepharose affinity chromatography on detergent extracts of [$^{125}$I]-surface-labeled untreated and RA/Bt$_2$cAMP-treated F9 cells was performed to isolate and characterize the HDL receptor of this invention. The results revealed that a number of radiolabeled polypeptides derived from the treated F9 cells bound to the HDL column. Prominent in the profile was a polypeptide with a M, of approximately 600 kDa. Immunoblot analysis of the eluted fraction using LRP-2/megalin antibody showed immunoreactive polypeptides having a molecular weight similar to that of the 600 kDa polypeptide observed in the autoradiograph.

In addition, there are a number of other polypeptides present in the elution profile from the treated but not from the untreated F9 cells. In particular, the profile of proteins eluted from the column using 8 mm urea contains four polypeptides having molecular weights of approximately 500, 400, 120 and 45 kDa. These polypeptides are not present in the corresponding profile of proteins derived from untreated cells.

To purify the receptor of this invention, HDL-Sepharose affinity chromatography can be performed by coupling lipid-depleted HDL to CNBr-activated Sepharose which can be used as an affinity matrix made free of ApoE-HDL or LDL by heparin-Sepharose absorption (i.e., an affinity matrix of delipidated HDL which is freed of ApoE-containing HDL or traces of LDL, whose presence may contribute to the undesired selection of apoE- and LDL binding receptors) to select HDL-binding proteins from detergent extracts of RA/Bt$_2$cAMP-treated F9 cells. Specifically, the cell extracts can be absorbed on columns of plain Sepharose and applied to separate columns of HDL (delipidated and absorbed on heparin-Sepharose) coupled to Sepharose. After washing, proteins bound to the HDL-Sepharose columns can be eluted in a sequential manner with 1, 4 and 8 M urease in 50 mM Tris (pH 7.5) buffer. The eluted proteins can be separated by SDS-PAGE followed by Coomassie blue staining and autoradiography. Any radiolabeled polypeptide(s) derived from the RA/Bt$_2$cAMP-treated F9 extracts that are not present in the profile derived from the control F9 cell extracts can be subjected to sequence analysis. In particular, the eluates can be electrophoresed on SDS-polyacrylamide gradient gels, transferred to PVDF membranes, stained with Coomassie blue and the bands excised. PVDF-immobilized polypeptides can be subjected to automated Edman degradation directly or can be proteolytically digested in situ (Argraves et al., 1990; Hunkapillar et al., 1983) and the resulting subfragments can be fractionated by microbore reverse phase HPLC and individually sequenced.

RAP-Sepharose Chromatography

RAP is an inhibitor of ligand binding for all members of the LDLR receptor family. The ability of RAP to inhibit the uptake of HDL by RA/Bt$_2$cAMP-treated F9 cells indicates that the HDL receptor is a RAP binding protein and may be a member of the LDL receptor family. RAP-Sepaharose chromatography of detergent extracts of [$^{125}$I]-cell surface labeled RA/Bt$_2$cAMP-treated F9 cells can be used to isolate RAP-binding receptors. RAP-Sepharose chromatography can also be performed on untreated F9 cells and RAP-Sepharose binding proteins from both types of cells can be eluted using EDTA and urea-containing buffers and evaluated by autoradiography after SDS-PAGE. Proteins selected as candidate HDL receptors on the basis of this comparison can be sequenced as described herein.

RAP-Sepharose bound proteins were eluted using 8M urea-containing buffer, separated by SDS-PAGE (non-reducing) and transferred to nitrocellulose membranes. The membranes were incubated with RAP (50 mM), followed by incubation with mouse monoclonal anti-RAP IgG and chemiluminescence agents and exposed to film.

The results indicate that a series of RAP-binding proteins are present in the RAP-Sepharose eluates from extracts of RA/Bt$_2$cAMP-treated and untreated F9 cells. However, these is a RAP-binding polypeptide having a molecular weight of approximately 400–500 kDa present only in the eluates derived from RA/Bt$_2$cAMP-treated F9 cell extracts. This polypeptide may be an HDL receptor on the basis that it has been shown that the process of HDL uptake by the differentiated F9 cells can be inhibited by RAP treatment. These data indicate that the HDL receptor is a RAP binding protein. Other RAP-binding proteins are common to eluates of both treated and untreated cells and may correspond to proteins such as the VLDL receptor and LRP-1.

Antibodies

Once the amino acid sequence of the polypeptide(s) of the receptor are determined, polyclonal and monoclonal antibodies can be produced according to protocols standard in the art for antibody production. HDL receptor-specific IgGs can be used in immunohistological staining experiments to characterize the pattern of HDL receptor expression in mammalian cells and tissues. The antibodies can also be tested in the screening assay of this invention for the ability to modulate the HDL binding and internalization activity of the HDL receptor.

Immuno-Blot Analysis

HDL-Sepaharose chromatography was performed as described herein using detergent extracts of RA/Bt$_2$cAMP-treated and untreated F9 cells. The extracts were applied to columns of apoHDL-Sepharose, washed with detergent buffer and then the bound proteins were eluted using 8M urea, 50 mM Tris, pH 7.4. Aliquots of peak fractions were electrophoresed on 4–12% polyacrylamide gradient gels (Novex) and electrophoretically transferred to nitrocellulose filter membranes. Unoccupied sites were blocked by incubation with 5% non-fat dry milk. Some of the filters were incubated with RAP, TBS (Tris buffered saline; 50 mM Tris, pH 7.4, 150 mM NaCl) (50 nM), or ovalbumin, TBC (50 nM), respectively and then incubated with mouse anti-RAP IgG and ECL detection reagents. Other filters were incubated respectively with mouse anti-LRP-2/megalin or rabbit anti-cubilin, followed by ECL detection reagents.

Experiments were performed to evaluate the effect of RA/Bt$_2$cAMP treatment on cubilin expression and these experiments showed that cubilin expression is induced by the RA/Bt$_2$cAMP treatment. The induction of cubilin expression correlates with the ability of RA/Bt$_2$cAMP-treated cells to mediate HDL uptake.

Experiments were also performed to evaluate the effect of serum on the process of HDL uptake by RA/Bt$_2$cAMP-treated cells. Serum deprivation reduced the level of cubilin and LRP-2/megalin in total cell extracts, however, the magnitude of reduction of LRP-2 expression was greater than that of cubilin.

It was also demonstrated that the cubilin antibody reacts with polypeptides present in HDL-Sepharose eluates from treated F9 cells but not untreated F9 cells. A major immunoreactive polypeptide corresponds exactly in size to the −500 kDa molecular weight subunit of the HDL receptor described herein. A higher molecular weight immunoreactive polypeptide of approximately 800 kDa was shown to bind anti-cubilin antibodies. This polypeptide corresponds in size to that of the cubilin dimer reported by Bim et al. (1997).

Nucleic Acids Encoding the HDL Receptor

Polymerase chain reaction (PCR)-based differential display methodologies as are known in the art can be used to identify cDNAs encoding the receptor of this invention. In particular, RNA can be isolated from cells producing the receptor, as identified by the methods described herein. Total RNA can be extracted from cells using a phenol/guanidinium thiocyanate extraction system (RNA Stat-60, Tel-test, Inc.).

To identify cDNAs corresponding to transcripts whose expression is increased in RA/Bt$_2$cAMP-treated cells as compared to control cells, protocols can be employed whereby the 3' ends of many different transcripts are amplified, based on the assumption that the HDL receptor cDNA will be a unique band present in the profile of PCR products derived from RNA of cells capable of endocytosing DiI-HDL, but not present in the profile of PCR products derived from RNA of cells that cannot internalize HDL. RT-PCR can be carried out using 80 different combinations of primer sets and [$\alpha$-$^{35}$S]-dATP (Qing et al., 1997). The primer sets can be composed of four degenerate anchored oligo(dT) primers, T$_{12}$MN (M is dG, dC or dA; N is dG, dC, dA or do) and 20 arbitrary 10 mers. The resulting PCR products can be separated by electrophoresis on 6% polyacrylamide gels and the resulting gels used for autoradiography. The banding pattern of cDNAs generated from the two RNA preparations can be compared. cDNAs present in the profile of products derived from RNA of cells capable of endocytosing DiI-HDL, but not present in the profile of products derived from cells that cannot internalize HDL, can be excised from the gels. These cDNAs can be used in RNA hybridization analysis to confirm that the corresponding mRNAs are indeed differentially expressed in the two RNA preparations (e.g., expressed exclusively or in greater abundance in RNA derived from the HDL receptor-positive cells). Subsequent sequence analysis can be performed to characterize the cDNAs.

On the basis that the HDL receptor of this invention may have similarities to members of the LDLR family, another approach to isolate cDNA encoding the HDL receptor can be employed. Specifically, homology-PCR cloning can be used to specifically amplify cDNAs corresponding to transcripts encoding all LDLR family members expressed by each cell population. This procedure involves preparing degenerate oligonucleotide primers (Konenberg et al., 1994) based on regions of protein sequence conserved across all LDLR family members that can universally prime cDNA production from all LDLR family member transcripts. In each oligonucleotide, inosine can be substituted at those positions having all four residues. Using the two RNA preparations (from HDL receptor positive and negative cells), template cDNA can be prepared using MMLV reverse transcriptase, random hexamer primers and dNTPs. PCR can then be performed using each of the template preparations, the above-mentioned degenerate primers and Taq polymerase as described (Konenberg et al., 1994). The PCR products can be ligated into the pCR-Script vector (Stratagene) and used to transform bacteria. Plasmids can be isolated from individual colonies and sequenced with an automated ABI 377 DNA Sequencer.

Another approach to isolate cDNAs encoding the HDL receptor of this invention is expression cloning which involves the transient expression of plasmid cDNA libraries in COS cells, such that cDNA-encoded proteins are expressed by the transfected cells, thereby enabling selection by exogenously added antibodies or ligands (Aruffo and Seed, 1987; Seed, 1995). Receptors that bind and internalize oxidized LDL (SR-BI and dSR-CI), as well as long chain fatty acid transporters have been identified by expression cloning (Acton et al., 1994; Pearson et al., 1995; Schaffer and Lodish, 1994). A plasmid cDNA library of cDNAs can be prepared from HDL receptor positive cell RNA, introduced into eukaryotic cells (e.g., COS or 293 cells) and screened for transfectants capable of mediating uptake of DiI-HDL, thereby allowing for the isolation of cDNAs which encode the HDL receptor of this invention.

To accomplish this, an expression cDNA library can be prepared according to standard protocols, consisting of $10^7$ unamplified clones or more from cDNA made from FAC-sorted HDL receptor positive cells and fractionated to a molecular mass cutoff of 700 bp. The cloning vector pEAK8 contains the EBV latent origin of replication and an EBNA-a transcription unit for plasmid replication in non-rodent cells and the SV40 origin for plasmid replication in cells expressing SV40 large T antigen. cDNA insertion can be by directional adaptor strategy. Insert expression is under the control of a modified version of the strong, cell-type independent EFI promoter. Transfectants can be selected by using approximately 1 μg/ml of puromycin. For maximum expression, 293-Twt cells are recommended by Edge Biosystems (Gaithersburg, Md.). Following the puromycin selection, the cells can be incubated with DiI-HDL and subjected to FAC sorting as described herein. Plasmids can be recovered from the FAC-sorted population of transfected cells that endocytose DiI-HDL by extraction with a buffer containing 1% SDS, 100 mM EDTA, 100 μg/ml proteinase K, 10 mM Tris, pH 8.0 at 55° C. as described by Davis et al. (1996). Samples can then be extracted with phenol/chloroform and ethanol precipitated. Plasmids can be further selected by three additional rounds of transfection and selection by DiI-HDL uptake and FAC sorting. The plasmids recovered from the 293-Twt cells can be used to transform bacteria; transformant colonies can be isolated and plasmid purified. Automated DNA sequence analysis can be performed on individual plasmid preparations according to standard protocols. Sequence analysis can be done using the GCG suite of programs. The technique of cDNA synthesis available from Edge BioSystems is reported to be optimized for producing long cDNAs (~7 kb).

Once the nucleic acid sequence of the cDNA encoding the HDL receptor in F9 cells is determined, the cDNA encoding the HDL receptor in human cells can be readily isolated and characterized. In particular, human cells which express the HDL receptor of this invention can be identified according to the methods provided herein. The RNA from human cells identified as producing the HDL receptor can be extracted and used to generate template cDNA which can be placed into plasmids and expressed in bacterial cells. The human cDNA can be probed with nucleic acid sequences from the F9 cDNA identified as described herein and human cDNA which hybridizes with the F9 cDNA can be sequenced to provide the nucleic acid encoding the HDL receptor of this invention. Additionally, any mammalian HDL receptor homologue can be identified and isolated according to the teachings provided herein.

Furthermore, vectors comprising nucleic acid encoding the HDL receptor of this invention can be introduced into cells to produce transfected cells which express the HDL receptor as an exogenous receptor. Such cells can be used in the screening methods of this invention to identify substances which can modulate the binding and internalization activity of the HDL receptor.

It is also contemplated in this invention that transgenic animals can be produced which either overproduce the HDL receptor of this invention or fail to produce the HDL receptor of this invention in a functional form. For example, a transgenic animal which overproduces the HDL receptor of this invention can be produced according to methods well known in the art whereby nucleic acid encoding the HDL receptor is introduced into embryonic stem cells, at which stage it is incorporated into the germline of the animal, resulting in the production of HDL receptor in the transgenic animal in increased amounts relative to a normal animal of the same species.

A transgenic animal in which the expression of HDL receptor is tissue specific is also contemplated for this invention. For example, transgenic animals that express or overexpress the HDL receptor at specific sites such as the liver can be produced by introducing a nucleic acid into the embryonic stem cells of the animal, wherein the nucleic acid is under the control of a specific promoter which allows expression of the nucleic acid in specific types of cells (e.g., a hepatic promoter which allows expression only in hepalic cells).

Alternatively, the transgenic animal of this invention can be a "knock out" animal (see, e.g., Willnow et al., 1996), which can be an animal that normally produces the HDL receptor but has been altered to prevent the expression of the animal's nucleic acid which encodes the HDL receptor, thereby resulting in an animal which does not produce the HDL receptor in a functional form. Such an animal may lack the ability to express all of the nucleic acids encoding the HDL receptor or the transgenic animal may lack the ability to express some (one or more than one) but not all of the nucleic acids encoding the HDL receptor.

For example, the transgenic "knock out" animal of this invention can have the expression of a gene or genes knocked out in specific tissues. This approach obviates viability problems that can be encountered if the expression of a widely expressed gene is completely abolished in all tissues. As a particular example, LRP is a member of the LDLR family whose expression is widespread in tissues of the embryo and adult. Complete knock out of LRP results in embryonic lethality. Using a cre-mediated approach, just the expression of LRP in the liver can be knocked out (Rohlmann et al., 1997). Such an approach can be used for the inactivation of HDL receptor expression at specific sites (e.g., in kidney proximal tubule cells).

Screening Assays

Identification of a substance having the ability to modulate the HDL binding and/or internalization function of the HDL receptor as determined by [$^{125}$I] internalization and degradation assay. The substance of interest can be contacted with cells producing the HDL receptor and then [$^{125}$I] labeled HDL can contacted with the cells and the amount of $^{125}$I HDL bound and internalized can be determined according to the protocols provided herein. A decrease or increase in the amount of [$^{125}$I] labeled HDL bound and internalized as compared to the amount of [$^{125}$I] labeled HDL bound and internalized by cells producing the HDL receptor and not contacted with the substance identifies a substance having the ability to modulate the HDL binding and/or internalization activity of the HDL receptor of this invention.

Example II

Identification of Cubilin as a Component of the HDL Receptor

Proteins

Human apolipoproteins apoA-I, apoA-II, apoC-1 and apoC-III were purified as described previously (Brewer et al., 1986; Jackson and Holdsworth 1986). Human apoE3 was purchased from Calbiochem (La Jolla, Calif.) and apoJ from Quidel (San Diego, Calif.). Recombinant human RAP was purified as described by Williams et al. (1992). Bovine serum albumin (BSA) was purchased from USB (Cleveland, Ohio). Ovalbumin and heparinase I were obtained from Sigma Chemical Co. (St. Louis, Mo.).

Lipoproteins

DiI-labeled human HDL, DiO-labeled human LDL and rabbit bVLDL were purchased from Biomedical Technologies (Stoughton, Mass.). Human HDL (d 1.0631–1.21 g/ml), $HDL_2$, $HDL_3$, delipidated HDL (apoHDL) and LDL were prepared as described (Kelly and Kruski 1986; Osborne 1986). DiI-HDL, HDL, apoHDL, $HDL_2$, and $HDL_3$ were depleted of apoE-HDL and other heparin-binding particles according to Oram (1986), dialyzed against 150 mM NaCl, 50 mM Tris pH 7.4 (TBS) containing 0.3 mM EDTA, filter-sterilized and stored at 4° C. Human Lp(a) was obtained from Dr. Peter Harpel (Mount Sinai Medical Center, New York, N.Y.), oxidized LDL from Dr. Alica Jenkins (Medical University of South Carolina, Charleston, S.C.), and human VLDL (S 100–400) from Dr. David Chappell (University of Iowa College of Medicine, Iowa City, Iowa). Lipoprotein concentration (µg protein/ml) was determined using BCA protein assay (Pierce, Rockford, Ill.).

Antibodies

IgGs from rabbit polyclonal anti-porcine LRP-2 (rb 6286) (Hammad et al., 1997) and anti-rat LRP-2 (rb 239) (Kounnas et al., 1994) were purified by protein-G-Sepharose affinity chromatography. Rabbit anti-cubilin serum and IgG were provided by Dr. Pierre Verroust (INSERM, Hospital Tenon, Paris, France). HRP-conjugated anti-rabbit IgG was obtained from Amersham (Buckinghamshire, England).

Cells

Mouse embryonal teratocarcinoma F9 cells (ATCC CRL 1720) were obtained from American Type Culture Collection. Differentiation of F9 cells was performed as described previously (Stefansson et al., 1995a). Briefly, F9 cells were seeded onto 0.1% gelatin-coated plastic tissue culture plates at $1 \times 10^2$ cells/cm$^2$ in Dulbecco's modified Eagle's medium (DMEM)(Mediatech, Hemdon, Va.) containing 10% iron-fortified bovine calf serum (BCS) (Hyclone, Logan, Utah), penicillin/streptomycin, 0.1 µM RA (Calbiochem, San Diego, Calif.), and 0.2 FM $Bt_2cAMP$ (Sigma). The cells were grown at 37° C., 5% $CO_2$ for 6 days without change of medium.

[$^{125}$I]HDL Binding, Intenralization and Degradation Assays

HDL internalization and degradation assays were performed as described previously for LDL and apolipoprotein J (Hammad et al., 1997; Kounnas et al., 1995; Stefansson et al., 1995a). ApoE-free HDL was labeled with [$^{125}$I]-iodine using the iodine monochloride method (Goldstein et al., 1983). RA/$Bt_2$cAMP-treated and untreated F9 cells were seeded into gelatin-coated 3.83 cM$^2$ wells (Corning, Corning, N.Y.) at $1.5-1.75 \times 10^5$ cells/well and allowed to grow for 18 h at 37° C., 5% $CO_2$ in serum-free medium (SFM) (DMEM containing ITS (insulin 5 µg/ml, transferrin 5 µg/ml, sodium selenite 5 ng/ml, Boehringer Mannheim, Germany), and penicillin/streptomycin). Prior to addition of radiolabeled HDL, the cells were washed with SFM and incubated in the assay medium (DMEM, 20 mM HEPES, ITS, penicillin/streptomycin, and 1.5% ovalbumin) alone or in the presence of unlabeled HDL (80 µg/ml), RAP (1 µM), chloroquine (50 µM), BSA (1 µM), anti-cubilin IgG (150 µg/ml) or control IgG (150 µg/ml) and incubated for 30 min at 37° C., 5% $CO_2$. The medium was then removed and radiolabeled apoE-free HDL (2 µg/ml) in assay medium alone or in assay medium containing unlabeled HDL (80 µg/ml), RAP (1 µM), chloroquine (50 µM), or BSA (10 µM) was added and incubated with the cells for 6.5 h at 37° C., 5% $CO_2$. The conditioned medium was treated with trichloroacetic acid (final concentration 10%) and centrifuged at 10,000×g for 10 min. The amount of radioactivity in the supernatant was taken to represent the amount of degraded HDL (Goldstein and Brown, 1974). The cell layer was washed three times with cold (4° C.) Dulbecco's phosphate buffered saline (DPBS) (Sigma) and then treated with 0.5 mg/ml trypsin-0.53 mM EDTA (Mediatech), 50 µg/ml proteinase K (Sigma) in dPBS (trypsin-EDTA-proteinase K) for 2–4 min at 4° C. The released cells were pelleted by centrifugation at 1,000×g for 15 min and the amount of radioactivity in the cell pellet was measured and taken to represent the amount of internalized HDL.

To study HDL binding to RA/$Bt_2$cAMP-treated F9 cells, a filter assay described previously (George et al., 1987; Schneider et al., 1979) for measuring binding of [$^{125}$I] LDL to adrenal cortex and oocyte extracts was adopted. Briefly, HDL binding sites present in an aliquot of RA/$Bt_2$cAMP-treated F9 cell CHAPS membrane extract were precipitated by adjusting the concentration of CHAPS to 2.5 mM. The precipitate was collected by centrifugation at 100,000×g for 1 h at 4° C. and resuspended in 100 mM NaCl, 2 mM $CaCl_2$, 50 mM Tris, pH 8.0 by aspiration through a 22-gauge needle. Aliquots of resuspended precipitate containing 45 µg of protein were combined with the indicated amounts of [$^{125}$I]-HDL and unlabeled HDL in a total volume of 100 µl (25 mM NaCl, 2 mM $CaCl_2$, 16 mg/ml BSA, 12.5 mM Tris-HCL, pH 8.0 final buffer composition) and incubated for 2 h at 24° C. Receptor-bound [$^{125}$I]-HDL was collected on 0.45-µm cellulose acetate filters (MSI, Minnetonka, Minn.) as described (Schneider et al., 1979). Binding data were fit to a single class of sites model using the computer program LIGAND (Munson and Rodbard 1980) and assuming a molecular mass for HDL of 200 kDa.

Measurement of DiI-HD, and DiO-LDL Uptake by Fluorescence-Activated Cell (FAC) Scanning RA/$Bt_2$cAMP-treated and -untreated F9 cells ($1-1.5 \times 10^5$ cells/cm$^2$) were grown for 18 h in SFM. After washing the cell layers with SFM, DiI-HDL or DIO-LDL was added to a final concentration of 1 µg/ml and incubated for 2 h at 37° C., 5% $CO_2$. For competition experiments, competitors (HDL, $HDL_2$, $HDL_3$ and their corresponding apoE-free forms), LDL, oxidized LDL, VLDL, §-VLDL, Lp(a) (100 mg/ml), apoA-I (28.3 µg/ml, 1 µM), apoA-II (I 7.3 µg/ml, 1 µM), apoC-I (6.6 µg/ml, 1 µM), apoC-III (8.8 µg/ml, 1 µM), apoJ (70 µg/ml, 1 µM), ovalbumin (45 µg/ml, 1 µM), RAP (39 µg/ml, 1 µM), apoE (8.5 µg/ml, 0.25 µM), heparin (80 µM, 250 U/ml) or IgGs (200 µg/ml) were added in SFM and incubated for 45 min at 37° C., 5% $CO_2$ prior to the addition of the fluorescent lipoproteins. After the incubation, the medium was removed, cell layers were washed with SFM and the cells were released with trypsin-EDTA-proteinase K. The cells were washed once with DMEM, twice with dPBS, then subjected to FAC scanning on a FACStar Plus instrument (Becton Dickinson, San Jose, Calif.). Plotted data are from gated cells having fluorescence intensity values greater than the autofluorescence values of 99% of unlabeled cells. For some experiments, cell layers were treated with hepaninase I (10 U/ml) for 2 h prior to the addition of the DiI-HDL. As a test of the effectiveness of this treatment, heparinase I was shown to reduce the levels of cell layer-associated [$^{35}$S]-sulfate by 50% that of controls using a method described by Mann et al. (1990).

HDL-Sepharose Affinity Chromatography

HDL-Sepharose affinity chromatography was performed using detergent extracts of RA/Bt$_2$cAMP-treated and -untreated F9 cells that were either cell surface [$^{125}$I]-labeled or non-radiolabeled. For radiolabeling, cells were washed three times with dPBS and detached using 2 mM EDTA in dPBS. The released cells were washed twice with DMEM then twice with dPBS. Cells (1×$_{10}$g) were radioiodinated using the lactoperoxidase/glucose oxidase method (Ashcom et al., 1990). After labeling, the cells were resuspended in 50 mM octyl-§-D-glucopyranoside (Calbiochem) in TBS containing 1 mM $CaCl_2$, 1 mM $MgCl_2$, 2 mM PMSF (OG buffer) and passed repeatedly through a 21-gauge needle. The extract was clarified by centrifugation at 100,000×g for 1 h. Extracts from each cell type were applied to columns of Sepharose-ClAB (5 ml) (Sigma) equilibrated with the OG buffer at 4° C. Sepharose CL4B-absorbed extracts were applied to columns of apoHDL (apoE-free) coupled to CNBr-activated-Sepharose (10 mg protein/ml resin). The columns were washed with OG buffer and the bound proteins eluted with sequential applications of 1, 4 and 8 M urea, 50 mM Tris pH 7.4. Peak fractions were pooled and dialyzed against TBS, 1 mM PMSF and absorbed on a column of wheat germ lectin-agarose (Pharmacia Biotech, Piscataway, N.J.). Bound proteins were eluted with 0.5 M N-acetyl-glucosamine in OG buffer, separated by SDS-PAGE (Novex, San Diego, Calif.) and analyzed by Coomassie blue staining and autoradiography.

Non-radiolabeled cells (1×10$^{9'}$) were released and washed as described above, then suspended in 0.25 M sucrose, 10 mM Hepes pH 7.4, containing a protease inhibitor cocktail (Complete, EDTA-free, Boehringer Mannheim). The cells were homogenized on ice using a Polytron homogenizer (Kinematica AG, Switzerland) at full speed for 2×30 seconds and the homogenates centrifuged at 2,000×g for 10 min. The resulting supernatants were centrifuged at 100,000×g for 1 h. The pellets were resuspended in 2 ml of CHAPS buffer (20 mM CHAPS (Sigma), 1 mM PMSF in TBS) by repeated passage through a 21-gauge needle. The extract was clarified by centrifugation at 100,000×g for 1 h. The concentration of protein in the final supernatants was determined and equal amounts of protein (20 mg) from each cell type were applied to columns of Sepharose-CL4B (5 ml) (Pharmacia) equilibrated with CHAPS buffer. Sepharose CL4B-absorbed extracts were applied to 6-ml columns of apoHDL-Sepharose and incubated 18 h at 4° C. with nutational movement. Bound proteins were eluted with 8 M urea buffer containing 50 mM Tris pH 7.4, separated by SDS-PAGE and analyzed by silver staining and immunoblotting.

Analysis of DiI-HDL Uptake by Cultured Cells and Mouse Yolk Sac Using Laser Scanning Confocal Fluorescence Microscopy Cells were plated into gelatin-coated wells of plastic chamber slides (Nalge Nunc, Naperville, Ill.) (4×10$^4$ cells/cm$^2$) and incubated at 37° C., 5% $CO_2$ for 2 h. The cells were washed and incubated in SFM for 18 h at 37° C., 5% $CO_2$. Prior to addition of fluorescent lipoproteins, the cells were preincubated with SFM containing HDL, LDL (40 µg/ml) or RAP (1 µM) for 45 min at 37° C., 5% $CO_2$. After the preincubation, DiI-HDL (1 µg/ml) and DiO-LDL (1 µg/ml) were added in SFM alone or in the presence of HDL, LDL (40 µg/ml) or RAP (1 pM) and incubated with the cells for 2 h at 37° C., 5% $CO_2$. The cells were washed with dPBS, fixed in 3% formaldehyde in dPBS for 20 min at 25° C. and analyzed using a BiORad MRC1024 laser scanning confocal microscope.

Embryos (8–8.5 days post-conception) were removed from timed pregnant ICR mice (Harlan Sprague Dawley, Inc.) so as to leave visceral yolk sac endoderm intact and placed in DMEM. The embryos were then incubated in DMEM containing RAP (1 µM), ovalbumin (1 µM), rabbit anti-cubilin IgG (400 µg/ml) or normal rabbit IgG (400 µg/ml) for 0.5 h at 37° C., 5% $CO_2$. DiI-HDL was added to a final concentration of (1 µg/ml) and incubated for 1 h at 37° C., 5% $CO_2$. The medium was removed and the embryos gently washed with dPBS and fixed with 3% paraformaldehyde for 15 min. The fixed embryos were placed in dPBS, 0.1% azide in a well slide and examined by laser scanning confocal microscopy. The intensity of yolk sac fluorescence in mouse embryos incubated with DiI-HDL in the presence of either RAP, ovalbumin, anti-cubilin IgG or control IgG was evaluated by seven people in a double blinded fashion. The assessments of relative intensity were analyzed by a nonparametric statistical test using RANK and ANOVA procedures (SAS Institute, Inc., Cary, N.C.).

In order to immunohistologically localize cubilin, embryos were fixed for IS min with 3% paraformaldehyde and permeablized for 30 min in 0.02% TritonX-100 in dPBS, 0.1% azide and then blocked for 12 h at 4° C. in 1% goat serum, PBS, 0.1% azide. The embryos were incubated with anti-cubilin IgG (10 µg/ml) in dPBS, 1% goat serum, 0.1% azide for 18 h at 4° C. The embryos were washed in dPBS, 0.1% azide for 18 h at 4° C. with gentle agitation and incubated 18 h with DTAF-labeled goat anti-rabbit IgG (Jackson ImmunOResearch Laboratories, West Grove, Pa.) in 1% goat serum. The embryos were washed and examined by laser scanning confocal microscopy.

During the course of evaluating lipoprotein metabolism (e.g., LDL uptake mediated by LRP-2/megalin (Stefansson et al., 1995)) in retinoic acid (RA)/dibutyryl cyclic AMP (BtrcAMP)-differentiated F9 cells, it was discovered that the cells had the capacity to internalize and degrade [$^{125}$I]-labeled HDL. The degradation of [$^{125}$I]-HDL occurred in lysosomes, as evidenced by the fact that chloroquine, a drug that inhibits lysosomal proteinase activity, effectively blocked the degradation. In addition, RAP, a 39-kDa protein that inhibits ligand binding to LDLR family members (Herz et al., 1991; Kounnas et al., 1992), inhibited the endocytosis and degradation of [$^{125}$I]-HDL. Undifferentiated F9 cells were unable to mediate HDL internalization and degradation. When detergent extracts of differentiated F9 cell membranes were analyzed for their ability to bind [$^{125}$I]-HDL by a solid-phase filter assay (Schneider et al., 1979), saturable and high affinity ($K_d=77\pm7$ nM, n=2) binding was observed.

Incubation of the RA/Bt$_2$cAMP-differentiated F9 cells with HDL labeled with DiI (a fluorescent lipid) produced a punctate subcellular staining pattern consistent with an endocytotic vesicle localization. The cell staining was blocked by addition of excess unlabeled HDL or RAP. An overlapping pattern of punctate fluorescent staining was observed, when the cells were incubated with both DiO-labeled LDL and DiI-HDL. The co-localization of the two labeled lipoproteins is an indication that HDL is trafficked through the same endocytic compartments as LDL. Undifferentiated F9 cells did not show staining after incubation with DiI-HDL, but did show punctate staining after incubation with DiO-LDL. Based on the results obtained using radiolabeled and fluorescent lipid-labeled HDL, it can be concluded that the RA/t$_2$cAMP-treated F9 cells express a receptor capable of mediating HDL endocytosis and lysosomal degradation. Furthermore, the fact that RAP can inhibit HDL endocytosis and degradation suggests that the HDL-endocytosis receptor is either a RAP-binding protein or that a RAP-binding member of the LDLR family is indirectly involved.

A fluorescence-activated cell scanning assay using DiI-HDL was developed to evaluate the specificity of HDL uptake by RA/Bt$_2$cAMP-differentiated F9 cells. HDL, subclasses HDL$_2$ HDL$_3$ and their apoE-free forms as well as HDL competed for HDL uptake. Using equal concentrations (w/v) of the HDL competitors, HDL$_3$ competed more effectively than HDL$_2$, irrespective of apoE content. To evaluate the apolipoprotein specificity, six HDL apolipoproteins were tested as competitors for DiI-HDL uptake. The major HDL apolipoprotein constituents, apoA-I and apoA-E, as well as apoE competed effectively for DiI-HDL uptake, whereas apoC-1, apoC-III and apoj displayed little or no ability to compete. Lipoprotein specificity of HDL uptake was evaluated and LDL, VLDL, §VLDL and Lp(a) showed little or no effect on HDL uptake. Similarly, oxidized LDL was unable to compete for HDL uptake. Since heparinase treatment has been shown to block apoE- and hepatic lipase-mediated uptake of HDL by cultured hepatocarcinoma cells (Zhong-Sheng et al., 1997), the effect of heparinase and heparin on DiI-HDL uptake by RA/Bt$_2$cAMP-differentiated F9 cells was evaluated. Neither heparin nor heparinase I pretreatment of RA/Bt$_2$cAMP-differentiated F9 cells inhibited DiI-HDL uptake. Taken together, the results demonstrate that the process of HDL uptake mediated by RA/Bt$_2$cAMP-differentiated F9 cells is highly specific, involving unique recognition of HDL and its apoA-I and/or apoA-II apolipoprotein moieties.

HDL-Sepharose chromatography was used to isolate the HDL holoparticle-endocytosis receptor from detergent extracts of RA/Bt$_2$cAMP-treated F9 cells. RA/Bt$_2$cAMP-treated F9 cells and -untreated F9 cells were surface-labeled with [$^{125}$I]-iodine, detergent-extracted and the extracts applied to columns of lipid-depleted HDL coupled to Sepharose. A major Coomassie-stainable, radiolabeled polypeptide of ~500 kDa and several minor polypeptides of 400, 116 and 45 kDa were present in the HDL-Sepharose eluates derived from the treated F9 cell extracts and not present in the eluates derived from the untreated cells.

LRP-2/megalin represented a candidate for the ~500-kDa HDL-Sepharose binding protein, given its similar size (520 kDa; Saito et al., 1994) and the fact that its expression was known to be augmented by RA/Bt$_2$cAMP treatment of F9 cells (Stefansson et al., 1995a). However, immunoblot analysis showed that the 500 kDa HDL-Sepharose-binding protein was not reactive with antibodies capable of detecting mouse LRP-2. Another candidate was cubilin, a 460-kDa RAP-binding receptor for intrinsic factor-vitamin B$_{12}$ complex (Birn et al., 1997; Moestrup et al., 1998; Seetharam et al., 1997). Not only did the size of cubilin correspond with that of the major HDL-Sepharose binding protein isolated from the RA/Bt$_2$cAMP-differentiated F9 cells, but there were other commonalities. For example, cubilin was known to be expressed by yolk sac endoderm cells (Sahali et al., 1988), the phenotype of RA/Bt$_2$cAMP-differentiated F9 cells, and cubilin had been shown to function as an endocytotic receptor (Bim et al., 1997; Seetharam et al., 1997). To test the possibility that the 500-kDa HDL-Sepharose binding protein corresponds to cubilin, immunoblot analyses were performed. Cubilin antibodies reacted with the 500-kDa HDL-Sepharose binding protein. The cubilin antibodies also reacted with an 800-kDa polypeptide present in the HDL-Sepharose eluate that corresponds to the previously described 800-kDa disulfide cross linked cubilin dimer (Birn et al., 1997). Cubilin antibodies did not react with any polypeptides present in the HDL-Sepharose eluate derived from the untreated F9 cells. The results indicate that cubilin is the major constituent present in the profile of HDL-Sepharose binding proteins isolated from RA/Bt$_2$cAMP-differentiated F9 cells.

To directly test the role of cubilin as an endocytotic receptor for HDL, cubilin antibodies were evaluated for their ability to block DiI-HDL and [$^{125}$I]-HDL internalization mediated by the RA/Bt$_2$cAMP-differentiated F9 cells. Cubilin antibodies effectively inhibited cellular uptake of DiI-HDL, but not DIO-LDL. Similarly, cubilin antibodies were found to effectively inhibit both the internalization and lysosomal degradation of [$^{125}$I]-HDL. The results support the conclusion that cubilin functions as an HDL holoparticle endocytosis receptor.

Given that LRP-21 megalin is highly expressed by differentiated F9 cells (Stefansson et al., 1995a) and that it has recently been found to be a cubilin-binding protein (Moestrup et al., 1998), the effect of LRP-2/megalin antibodies on DiI-HDL uptake was evaluated. LRP-2 antibodies (rb6286) did not block DiI-HDL uptake, but were capable of blocking uptake of DiO-LDL to a level comparable to that achieved using excess LDL as a competitor. Similarly, antibodies from another LRP-2/megalin antiserum (rb239) did not inhibit DiI-HDL uptake.

The yolk sac endoderm mediates uptake of maternal-derived HDL (Woollett 1996; Wyne and Woollett 1998) and is a major site of cubilin expression (Sahali et al., 1988). To determine whether yolk sac uptake of HDL is mediated by cubilin, experiments were performed using ex utero mouse embryo culture. Mouse embryos having intact visceral yolk sacs were incubated in medium containing DiI-HDL with or without antagonists of cubilin activity, RAP or anti-cubilin IgG. In the absence of any antagonist, DiI-HDL became incorporated exclusively within the visceral extraembryonic yolk sac endoderm. Little or no DiI-HDL was detected within the intraembryonic endoderm. Consistent with these findings, immunostaining of embryos with cubilin antibodies revealed that cubilin is expressed by the visceral extraembryonic endoderm, but not the intraembryonic endoderm. When RAP was co-incubated with DiI-HDL, compared to the control protein ovalbumin, there was a significant reduction ($p<0.01$) in the incorporation of the DiI-HDL into extraembryonic endoderm as indicated by fluorescence intensity RANK scores $9.77\pm0.22$ S.D and $4.16\pm0.15$ S.D. for RAP and ovalbumin treatment, respectively. When cubilin antibodies were co-incubated with DiI-HDL, there was also a significant decrease ($p<0.01$) in the incorporation of the labeled HDL into extraembryonic endoderm compared to co-incubation of DiI-HDL with control IgG as indicated by RANK scores of 9.16±0.41 S.D and 3.83±0.41 S.D., respectively.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

Gordon, D J and Rifkind, B M 1989. High density lipoprotein—the clinical implications of recent studies. *N. Engl. J. Med.* 321:1311–1316.

Assmanin, G and Schulte, H 1992. Relation of high density lipoprotein cholesterol and triglycerides to incidence of atherosclerotic coronary artery disease (the PROCAM experience). Prospective Cardiovascular Munster study. *Am J. Cardiol.* 70:733–737.

Stampfer, M J, Sacks, F M, Salvini, S, Willett, W C and Hennekens, C H 1991. A prospective study of cholesterol, apolipoproteins, and the risk of myocardial infarction. *N. Engl. J. Med.* 325:373–381.

Rubin, E M, Krauss, R M, Spangler, E A, Verstufyt, J G and Clift, S M 1991. Inhibition of early atherogencsis in transgenic mice by human apolipoprotein A1. *Nature* 353:265–267.

Rohlmann A, Gotthardt M, Hammer R E, Herz J. 1998. Inducible activation of hepatic LRP gene by cre-mediated recombination confirms role of LRP in clearance of chylomicron remnants. *J Clin. Invest.* 101 (3):689–695.

Saito A, Pietromonaco S, Loo A K, Farquhar M G. 1994. Complete cloning and sequencing of rat gp330/"megalin," a distinctive member of the low density lipoprotein receptor gene family. *Proc. Natl. Acad. Sci. USA* 91(21):9725–9729.

Willnow T E, Hilpert J, Armstrong S A, Rohlmami A, Hammer R E, Burns D K, Herz J. 1996. Defective forebrain development in mice lacking gp330/megalin. *Proc. Natl. Acad. Sci. USA.* 93(16):8460–8464.

Eisenberg S. 1984. High density lipoprotein metabolism. *J. Lipid Res.* 25:1017–1058.

Tall A R. 1990. Plasma high density lipoproteins. Metabolism and relationship to atherogenesis. *J. Clin. Invest.* 86:379–384.

Woollett L A. 1996. Origin of cholesterol in the fetal golden Syrian hamster: contribution of de novo sterol synthesis and maternal-derived lipoprotein cholesterol. *J. Lipid Res.* 37:1246–1257.

Moestrup S K et al. 1998. The intrinsic factor-vitamin $B_{12}$ receptor and target of teratogenic antibodies is a megalin-binding peripheral membrane protein with homology to developmental proteins. *J. Biol. Chem.* 273(9):5235–5242.

Lewin, "Genes V" Oxford University Press Chapter 1, pp. 9–13 (1994).

Harlow and Lane. Antibodies, A Laboratory Manual. Cold Spring Harbor Laboratory, Cold Spring Harbor, N.Y., 1988.

Sambrook et al., *Molecular Cloning: A Laboratory Manual.* 2nd Ed., Cold Spring Harbor Laboratory, Cold Spring Harbor, N.Y. (1989).

Kohler, G. et at., "Continuous cultures of fused cells secreting antibody of predefined specificity." *Nature* 256:495–97 (1975).

Lewin, "Genes V" Oxford University Press Chapter 7, pp. 171–174 (1994).

Michieli, P., Li, W., Lorenzi, M. V., Miki, T., Zakut, R., Givol, D., and Pierce, J. H. (1996) *Oncogene* 12, 775–784.

Kunkel et al., *Methods Enzymol.* 154:367 (1987).

Brake et al., 1984. Alpha-factor-directed synthesis and secretion of mature foreign proteins in *Saccharomyces cerevisiae*. *PNAS* 82:4642–4646.

Bim H., et al. 1997. Characterization of an epithelial; 460-kDa protein that facilitates endocytosis of intrinsic factor-vitamin $B_{12}$ and binds receptor-associated protein. *J. Biol. Chem.* 272(42):26497–26504.

Sahali D., et al. 1992. Coexpression in humans by kidney and fetal envelopes of a 280 kDa-coated pit-restricted protein. Similarity with the murine target of teratogenic antibodies. *Am. J. Pathol.* 140(1):33–44.

Brewer, H B., et al. 1986. Isolation and characterization of apoliproteins A-1, A-II and A-IV. *Methods in Enzymol.* 128:223–244.

Oram J F. 1986. Receptor-mediated transport of cholesterol between cultured cells and high density lipoproteins. *Methods in Enzymol.* 129:645–659.

Goldstein, J L., et al. 1983. Receptor-mediated endocytosis of low density lipoprotein in cultured cells. *Methods in Enzymol.* 98:241–260.

Goldstein J L and Brown M S. 1974. Binding and degradation of low density lipoproteins by cultured human fibroblasts. Comparison of cells from a normal subject and from a patient with homozygous familial hypercholesterolemia. *J. Biol. Chem.* 249:5153–5162.

Kounnas M Z, et al. 1995. Identification of glycoprotein 330 as an endocytotic receptor for apolipoprotein J/clusterin. *J. Biol. Chem.* 270:13070–13075.

Stefansson S, et al. 1995. Glycoprotein 330/low density lipoprotein receptor-related protein-2 mediates endocytosis of low density lipoproteins via interaction with apolipoprotein B100. *J. Biol. Chem.* 270:19417–19421.

Ashcom J D, et al. 1990. The human alpha 2-macroglobulin receptor: identification of a 420 kDa cell surface glycoprotein specific for the activated conformation of alpha 2-macroglobulin. *J. Cell Biol.* 110: 1041–1048.

Qing J, et al. 1997. Suppression of anchorage-independent growth and matrigel invasion and delayed tumor formation by elevated expression of fibulin-1D in human fibrosarcoma-derived cells lines. *Oncogene* 15:

Korenberg J R, et al. 1994. Chromosomal localization of human genes for the LDL receptor family member glycoprotein 330 (LRP2) and its associated protein RAP (LRPAPI). *Genomics* 22:88–93.

Aruffo A and Seed B, 1987. Molecular cloning of a CD28 cDNA by a high efficiency COS cell expression system. *Proc. Natl. Acad. Sci. USA* 84:8573–8577.

Seed B. 1995. Developments in expression cloning. *Current Opinion in Biotechnology* 6:567–573.

Acton S L, et al. 1994. Expression cloning of SR-BI, a CD36related class B scavenger receptor. *J. Biol. Chem.* 269:1003–21009.

Pearson A, et al. 1995. Expression cloning of dSR-CI, a class C macrophage-specific scavenger receptor from *Drosophila melanogaster*. *Proc. Natl. Acad. Sci. USA.* 92:4056–4060.

Schaffer J E and Lodish H F. 1994. Expression cloning and characterization of a novel adipocyte long chain fatty acid transport protein. *Cell* 79:427–436.

Davis S, et al. 1996. Isolation of angiopoietin-1, a ligand for the TIE2 receptor, be secretion-trap expression cloning. *Cell* 87:1161–1169.

Argraves W S, et al. 1990. Fibulin is an extracellular matrix and plasma glycoprotein with repeated domain structure. *J. Cell Biol.* 111:3155–3164.

Hunkapillar M W, et al. 1983. Isolation of microgram quantities of proteins from polyacrylamide gels for amino acid sequence analysis. *Methods Enzymol.* 91:227–236.

Battey F D, et al. 1994. The 39-kDa receptor-associated protein regulates ligand binding by the very low density lipoprotein receptor. *J. Biol. Chem.* 269:23268–23273.

Bu G, et al. 1995. 39 kDa receptor-associated protein is an ER resident protein and molecular chaperone of LDL receptor-related protein. *EMBO J.* 14:2269–2280.

Herz 1, et al. 1991. 39-kDa protein modulates binding of ligands to low density lipoprotein receptor-related protein/ alpha 2-macroglobulin receptor. *J. Biol. Chem.* 266:21232–21238.

Kounnas M Z, et al. 1992. The 39-kDa receptor-associated protein interacts with two members of the low density lipoprotein receptor family, alpha 2-macroglobulin receptor and glycoprotein 330. *J. Biol. Chem.* 267:21162–21166.

Williams S E, et al. 1992. A novel mechanism for controlling the activity of alpha 2-macroglobulin receptor/low density lipoprotein receptor-related protein. Multiple regulatory sites for 39-kDa receptor-associated protein. *J. Biol. Chem.* 267:9035–9040.

Batuman V, et al. 1998. Myeloma light chains are ligands for cubilin (gp280). *Am. J. Physiol.* 275:F246–254.

Le Panse S, et al. 1995. Immunofunctional properties of a yolk sac epithelial cell line expressing two proteins gp280 and gp330 of the microvillar area of proximal tubule cells: inhibition of endocytosis by the specific antibodies. *Eur. J. Cell Biol.* 67:120–129.

Vandeputte M, et al. 1979. Endodermal antigen(s) in yolk sac derived teratomas. In: H. Peeters (ed.), *Protides of the Biological Fluids.* 27th Colloquium, pp. 179–183. Pergamon Press, Oxford.

George, R., Barber, D. L., and Schneider, W. J. (1987). Characterization of the chicken oocyte receptor for low and very low density lipoproteins. *J Biol Chem* 262, 16838–16847.

Hammad, S. M., Ranganathan, S., Loukinova, E., Twal, W. O., and Argraves, W. S. (1997). Interaction of apolipoprotein J-amyloid beta-peptide complex with low density lipoprotein receptor-related protein-2/megalin. A mechanism to prevent pathological accumulation of amyloid beta-peptide. *J Biol Chem* 272, 18644–18649.

Herz, J., Goldstein, J. L., Strickland, D. K., Ho, Y. K., and Brown, M. S. (1991). 39-kDa protein modulates binding of ligands to low density lipoprotein receptor-related protein/ alpha 2-macroglobulin receptor. *J Biol Chem* 266, 21232–21238.

Jackson, R. L., and Holdsworth, G. (1986). Isolation and properties of human apolipoproteins C-I, C-II, and C-III. *Methods Enzymol* 128, 288–296.

Kelly, J. L., and Kruski, A. W. (1986). Density gradient ultracentrifugation of serum lipoproteins in a swinging bucket rotor. *Methods Enzymol* 128, 170–180.

Kounnas, M. Z., Haudenschild, C. C., Strickland, D. K., and Argraves, W. S. (1994). Immunological localization of glycoprotein 330, low density lipoprotein receptor related protein and 39 kDa receptor associated protein in embryonic mouse tissues. *In Vivo* 8, 343–351.

Mann, D. M., Yamaguchi, Y., Bourdon, M. A., and Ruoslahti, E. (1990). Analysis of glycosaminoglycan substitution in decorin by site-directed mutagenesis. *J Biol Chem* 265, 5317–5323.

Munson, P. J., and Rodbard, D. (1980). Ligand: a versatile computerized approach for characterization of ligand-binding systems. *Anal Biochem* 107, 220–239.

Osborne, J. C. (1986). Delipidation of plasma lipoproteins. *Methods Enzymol* 128, 213–222.

Sahali, D., Mulliez, N., Chatelet, F., Dupuis, R., Ronco, P., and Verroust, P. (1988). Characterization of a 280-kDa protein restricted to the coated pits of the renal brush border and the epithelial cells of the yolk sac. Teratogenic effect of the specific monoclonal antibodies. *J Exp Med* 167, 213–218.

Schneider, W. J., Basu, S. K., McPhaul, M. J., Goldstein, J. L., and Brown, M. S. (1979). Solubilization of the low density lipoprotein receptor. *Proc Natl Acad Sci USA* 76, 5577–5581.

Seetharam, B., Christensen, E. I., Moestrup, S. K., Hammond, T. G., and Verroust, P. J. (1997). Identification of rat yolk sac target protein of teratogenic antibodies, gp280, as intrinsic factor-cobalamin receptor. *J Clin Invest* 99, 2317–2322.

Williams, S. E., Ashcom, J. D., Argraves, W. S., and Strickland, D. K. (1992). A novel mechanism for controlling the activity of alpha 2-macroglobulin receptor/low density lipoprotein receptor-related protein. Multiple regulatory sites for 39-kDa receptor-associated protein. *J Biol Chem* 267, 9035–9040.

Woollett, L. A. (1996). Origin of cholesterol in the fetal golden Syrian hamster: contribution of de novo sterol synthesis and maternal-derived lipoprotein cholesterol. *J Lipid Res* 37, 1246–1257.

Wyne, K. L., and Woollett, L. A. (1998). Transport of maternal LDL and HDL to the fetal membranes and placenta of the Golden Syrian hamster is mediated by receptor-dependent and receptor-independent processes. *J Lipid Res* 39, 518–530.

What is claimed is:

1. A method of screening a substance for the ability to modulate high density lipoprotein (HDL) holoparticle binding and/or internalization activity of an isolated mammalian receptor which specifically binds an HDL holoparticle, comprising:

a) contacting the substance with a cell producing a functional HDL receptor, and b) assaying the cell for a modulation of the HDL holoparticle binding and/or internalization activity of the receptor, whereby a modulation of the HDL holoparticle binding and/or internalization activity of the receptor identifies a substance with the ability to modulate the HDL holoparticle binding and/or internalization activity of the HDL receptor, wherein a functional HDL receptor comprises, as measured by sodium dodecyl sulfate-polyacrylamide gel electrophoresis (SDS-PAGE) under non-reducing conditions:

(i) a subunit of approximately 450,600 kDa molecular weight, wherein the 450–600 kDa molecular weight subunit is cubilin, and one or more subunits selected from the group consisting of a subunit of approximately 40–50 kDa molecular weight, a subunit of approximately 120 kDa molecular weight and a subunit of approximately 400 kDa molecular weight;

(ii) a subunit of approximately 800 kDa molecular weight and one or more subunits selected from the group consisting of a subunit of approximately 40–50-kDa molecular weight, a subunit of approximately 120 kDa molecular weight and a subunit of approximately 400 kDa molecular weight;

(iii) a subunit of approximately 400 kDa molecular weight and one or more subunits selected from the group consisting of a subunit of approximately 40–50 kDa molecular weight and a subunit of approximately 120 kDa molecular weight; or (iv) a subunit of approximately 120 kDa molecular weight and a subunit of approximately 40–50 kDa molecular weight.

2. The method of claim 1, wherein the assay for modulation of the HDL holoparticle binding and/or internalization activity of the receptor is selected from the group consisting of an HDL holoparticle receptor binding assay, an HDL holoparticle internalization assay; an HDL holoparticle degradation assay, an assay which detects modulation in the HDL holoparticle binding and/or internalization activity of the receptor as a result of a decrease or increase in the amount of HDL receptor-encoding mRNA produced by a cell, an assay which detects modulation in the HDL holoparticle binding and/or internalization activity of the receptor as a result of an increase or decrease in the amount of functional HDL receptor protein produced by a cell and a receptor recycling assay.

3. The method of claim 2, wherein the cell producing the functional HDL receptor is an F9 cell.

* * * * *